US011191596B2

(12) United States Patent
Thompson et al.

(10) Patent No.: US 11,191,596 B2
(45) Date of Patent: Dec. 7, 2021

(54) FOOT CONTROLLER

(71) Applicant: Intuitive Surgical Operations, Inc., Sunnyvale, CA (US)

(72) Inventors: Allen C. Thompson, Los Altos, CA (US); Scott O. Luke, Ben Lomond, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 331 days.

(21) Appl. No.: 16/191,208

(22) Filed: Nov. 14, 2018

(65) Prior Publication Data

US 2019/0142530 A1    May 16, 2019

Related U.S. Application Data

(60) Provisional application No. 62/586,356, filed on Nov. 15, 2017.

(51) Int. Cl.
*G05B 15/00*    (2006.01)
*A61B 34/00*    (2016.01)
(Continued)

(52) U.S. Cl.
CPC .............. *A61B 34/25* (2016.02); *A61B 34/35* (2016.02); *A61B 34/37* (2016.02); *G05G 1/305* (2013.01);
(Continued)

(58) Field of Classification Search
CPC ......... A61B 34/25; A61B 34/37; A61B 34/35; A61B 90/361; A61B 2017/00973;
(Continued)

(56) References Cited

U.S. PATENT DOCUMENTS 5,257,890 A * 11/1993 Vickary .................... B66F 9/02
                                                        414/420
6,260,434 B1 * 7/2001 Holtorf ..................... G05G 1/30
                                                         74/478
(Continued)

FOREIGN PATENT DOCUMENTS

WO    WO-0214970 A2    2/2002
WO    WO-2015052051 A1    4/2015

OTHER PUBLICATIONS

EYE4VISION Int'l, Cold Phaco Mode—Foot Pedal Controls, 2017, Retrieved from the Internet: URL: http://www.eye4vision.com/footpedal_cold_phaco_mode.html>, 1 page.
(Continued)

*Primary Examiner* — B M M Hannan
(74) *Attorney, Agent, or Firm* — IP Spring

(57) ABSTRACT

A foot controller includes a stationary portion and a cradle member that can receive a foot of a user. The cradle member is moveable to of different positions along paths, such as a left position, a right position, a front position, or a back position. One or more paths have a left-right direction of the controller and at least one of the paths has a forward-back direction of the controller. Sensors sense the cradle member at a particular position and output sensor signals indicative of that position. A function provided by a system is activated based on the sensed position.

20 Claims, 21 Drawing Sheets

(51) Int. Cl.
  *A61B 34/35* (2016.01)
  *G06F 3/033* (2013.01)
  *G06F 3/01* (2006.01)
  *A61B 34/37* (2016.01)
  *G05G 1/30* (2008.04)
  *A61B 90/00* (2016.01)
  *A61B 17/00* (2006.01)

(52) U.S. Cl.
  CPC ............ *G06F 3/016* (2013.01); *G06F 3/0334* (2013.01); *A61B 34/74* (2016.02); *A61B 34/76* (2016.02); *A61B 90/361* (2016.02); *A61B 2017/00973* (2013.01); *G05G 1/30* (2013.01)

(58) Field of Classification Search
  CPC ......... A61B 34/76; A61B 34/74; A61B 34/30; A61B 34/70; G06F 3/016; G06F 3/0334; G05G 1/305; G05G 1/30
  USPC ........................................................ 700/258
  See application file for complete search history.

(56) References Cited

U.S. PATENT DOCUMENTS

| | | | | |
|---|---|---|---|---|
| 6,452,120 | B1* | 9/2002 | Chen ...................... | G05G 1/30 200/52 R |
| 6,452,123 | B1* | 9/2002 | Chen ...................... | G05G 1/30 200/86.5 |
| 8,120,301 | B2 | 2/2012 | Goldberg et al. | |
| 10,349,925 | B2* | 7/2019 | Wong ..................... | A61B 90/98 |
| 10,401,893 | B2* | 9/2019 | Dumitrescu ............. | G05G 5/08 |
| 2003/0047434 | A1* | 3/2003 | Hanson .................. | A61B 17/00 200/86.5 |
| 2003/0114962 | A1* | 6/2003 | Niemeyer .......... | A61B 1/00149 700/245 |
| 2011/0092887 | A1* | 4/2011 | Wong ..................... | A61B 90/98 604/22 |
| 2011/0098721 | A1* | 4/2011 | Tran ....................... | A61B 34/20 606/130 |
| 2011/0118748 | A1* | 5/2011 | Itkowitz ................. | A61B 34/37 606/130 |
| 2015/0051607 | A1* | 2/2015 | Hajishah ................ | A61B 90/98 606/107 |
| 2015/0355669 | A1* | 12/2015 | Dumitrescu ............. | G05G 1/44 74/478 |
| 2017/0007218 | A1* | 1/2017 | Lai ........................ | G05G 1/305 |
| 2017/0095298 | A1 | 4/2017 | Vakharia et al. | |
| 2018/0078034 | A1* | 3/2018 | Savall ..................... | B25J 9/1689 |
| 2018/0078319 | A1* | 3/2018 | Nobles .................... | A47C 1/00 |
| 2018/0083621 | A1* | 3/2018 | Ekvall ................... | H03K 17/975 |
| 2018/0132948 | A1* | 5/2018 | Mercado ................. | G01L 5/161 |
| 2018/0280099 | A1* | 10/2018 | Cone ...................... | G05G 1/445 |

OTHER PUBLICATIONS

EYE4VISION Int'l, Phacoemulsification System—Foot Pedal Controls, retrieved on Jan. 15, 2017, Retrieved from the Internet: URL: http://www.eye4vision.com/phacoemulsification_system_footpedal.html>, 1 page.

Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

XO Care, Technical Specifications, retrieved on Jan. 15, 2017, Retrieved from the Internet: URL: https://www.xo-care.com/technical-specifications/>, 14 pages.

XO Care, The Ergonomics of Dental Foot Controllers, Jan. 12, 2015 [retrieved on Nov. 15, 2018]. Retrieved from the Internet: URL: https://www.xo-care.com/journal/the-ergonomics-of-dental-foot-controllers/#>, 4 pages.

\* cited by examiner

300

700

FOOT CONTROLLER

CROSS-REFERENCE TO RELATED APPLICATIONS

The present application claims priority to U.S. Provisional Patent Application No. 62/586,356, filed Nov. 15, 2017 and titled "Foot Controller," the entire contents of which are hereby incorporated by reference.

BACKGROUND

In teleoperated operations such as teleoperated surgery, a user (e.g., surgeon) typically operates a master controller, e.g., via a workstation, to remotely control (e.g., teleoperate) the motion and functions of instruments at a work site (e.g., surgical site or patient). The workstation may be separated from the patient by a significant distance (e.g., across an operating room, in a different room, or in a completely different building than the patient). Alternatively, a workstation may be positioned near the patient in the operating room. The master controller utilizes master controls, which will typically include one or more hand input devices such as pincher grips, joysticks, exo-skeletal gloves, or the like. These hand input devices are in communication with the surgical instrument. More specifically, a manipulator or slave device including a surgical instrument is moved based on the surgeon's manipulation of the hand input devices. During a surgical or other medical operation, the hand controller may control, via the teleoperated surgery system, a variety of surgical instruments such as tissue graspers, needle drivers, electrosurgical cautery probes, etc. Each of these instruments performs functions for the surgeon, for example, holding or driving a needle, grasping a blood vessel, or dissecting, cauterizing, or coagulating tissue. Some teleoperated surgical systems employ one or more foot switches or foot pedals to allow the user to control additional functions of various instruments and devices with his or her foot during a surgical procedure.

SUMMARY

Implementations of the present application relate to a foot controller. In some implementations, a controller includes a stationary portion and a cradle member coupled to the stationary portion and configured to receive a foot of a user. The cradle member is moveable to a plurality of positions along paths, where one or more of the paths have a component direction along a left-right axis of the controller and one or more of the paths have a component direction along a forward-back axis of the controller. The plurality of positions include one or more of a left position, a right position, a front position, or a back position. One or more sensors are operative to sense the cradle member at a particular position of the plurality of positions and output one or more sensor signals indicative of the particular position, where the one or more sensor signals cause activation of a selected function of a plurality of functions provided by a system in communication with the one or more sensors based on the particular position at which the cradle member is sensed.

Various implementations and examples of the controller are described. For example, in some implementations, the controller further includes a base member coupled between the cradle member and the stationary portion, where the cradle member is moveable with respect to the base member along a first one of the left-right axis and the forward-back axis, and the base member is moveable with respect to the stationary portion along a second one of the left-right axis and the forward-back axis. In some examples, the cradle member is moveable along the forward-back axis, and the base member is moveable along the left-right axis. The base member can be configured to pivot about a pivot axis to enable movement of the cradle member in the left-right axis, where the pivot axis is perpendicular to a plane of movement of the cradle member.

In some implementations, the cradle member is physically biased to move to a particular position. In some implementations, the paths are predetermined paths, and a guide is engaged with the cradle member, where the guide limits movement of the cradle member to the predetermined paths. In some examples, the guide includes a plate having slots that define the predetermined paths. Each of the plurality of positions can correspond to one of the plurality of functions, and the plurality of functions can include a plurality of different functions. The cradle member can include at least one input control provided on the cradle member that is configured to be activated by at least a portion of the foot of the user to output a control signal to the system. In some implementations, the cradle member can include protrusions on left and right sides of the cradle member, where the protrusions can receive a side of a user's foot when the cradle member is translated at least partially along the left-right axis. Some implementations include one or more actuators coupled to the cradle member (and/or the base member), where the one or more actuators are configured to output one or more forces in one or more of the paths. In some implementations, the system in communication with the sensor includes a surgical system having one or more surgical instruments, including cameras, and wherein the plurality of functions include at least one of: activating a function of at least one of the one or more surgical instruments, or switching user control between the one or more surgical instruments.

In some implementations, a system includes one or more processors, one or more slave instruments, where the one or more processors are configured to control the one or more slave instruments, and a foot controller. The foot controller includes a stationary portion and a cradle member and a base member coupled to the stationary portion and configured to receive a foot of a user, where the cradle member is constrained to move to a plurality of positions along paths. One or more of the paths have a component direction along a left-right axis and one or more of the paths have a component direction along a forward-back axis. In some implementations, the paths may include a direction at least partially along a left-right axis as left/right motion that includes a pivoting motion about the heel of the foot. The plurality of positions include one or more of a left position, a right position, a front position, or a back position. One or more sensors are operative to sense the cradle member at a particular position of the plurality of positions and output one or more sensor signals indicative of the particular position. The sensor signals are provided to the one or more processors to cause activation of a selected function of a plurality of functions associated with the one or more slave instruments based on the particular position at which the cradle member is sensed.

Various implementations and examples of the system are described. For example, in some implementations, each of the plurality of positions corresponds to one of the plurality of functions, the plurality of functions includes a plurality of different functions, and the cradle member includes an input control operative to send a control signal to the one or more processors. In some implementations, the paths are predetermined paths, and the foot controller further includes a guide engaged with the cradle member, the guide including a plurality of slots that limit movement of the cradle member to the predetermined paths. In some implementations, a restoring force can physically bias the cradle member to move to a center position of the cradle member along the left-right axis and/or the forward-back axis, where the restoring force is provided by a mechanism coupled to the cradle member. In some implementations, the mechanism includes a cam and a cam follower. In some implementations, the plurality of functions associated with the slave instruments include a swap function that swaps user control between a first one of the slave instruments and a second one of the slave instruments, a slave instrument function (e.g., a cutting function, an energy function, an irrigation function, a suction function, and a grasping function, etc.), and/or a clutch function that causes engagement and/or disengagement of user control of at least one of the slave instruments.

In some implementations, a method includes receiving a foot of a user in a cradle member of a controller, where the cradle member is moveable by the foot of the user into a plurality of positions including one or more of a left position, a right position, a front position, or a back position. The method includes constraining movement of the cradle member to paths to the plurality of positions, where one or more of the paths have a component direction along a left-right axis and one or more of the paths have a component direction along a forward-back axis. The method includes sensing the cradle member at a particular position of the plurality of positions, and outputting one or more sensor signals indicative of the particular position, where the sensor signals cause activation of a selected function of a plurality of functions of a device (e.g., a slave device) based on the one or more sensor signals.

Various implementations and examples of the method are described. For example, in some implementations, constraining the movement of the cradle member uses a guide engaged with the cradle member, where the guide includes a plate having a plurality of slots that limit movement of the cradle member to the predetermined paths. The method can further include causing selective output of force in at least two of the paths by one or more actuators coupled to the cradle member, where the force provides a different force effect in each of a plurality of the at least two of the paths. In some implementations, the cradle member includes an input control, and the method further includes sensing activation of the input control by the foot of the user, causing activation of one or more slave instrument actions associated with one or more of the functions.

DETAILED DESCRIPTION

Implementations relate to a foot controller. As described in more detail herein, implementations provide a foot controller enabling accurate user control over multiple functions of a system using the user's foot. For example, described features allow a user to select various functions at different activation positions of a moveable foot cradle of the foot controller, where the food cradle can be guided along different particular paths to reach the activation positions quickly and easily. The foot cradle and other controls of the foot controller can be depressed, slid, and/or otherwise manipulated by a user's foot to input various commands to a controlled system while the user is sitting or standing. Functions activated at the activation positions can include, in some implementations, functions associated with surgical tools and other instruments used in treating patients, including instruments used in teleoperated systems. In various implementations, surgical instruments may include image capture devices, e.g., cameras for use with surgical procedures. Various described features of the foot controller include mechanisms enabling customizable and programmable paths of the foot cradle, restoration of the foot cradle to an origin position, output of forces and haptic sensations to the foot cradle, and other features providing accurate and safe selection of functions using the foot controller.

Some implementations provide a foot controller adapted to operation by a user in a standing position, where the single foot controller described herein can enable functionality provided by multiple foot controls in previous use. In some example circumstances, a user can be positioned in a standing position close to a patient or other site. For example, a user can use one or more hand controllers while operating one or more foot controllers. Some implementations utilize a single foot controller for a user that is standing on one foot and operating the foot controller with the other foot. For example, the controlling foot can be supported at the heel of the controlling foot, such that the controlling foot and foot cradle member can pivot laterally, from side to side.

Various terms including "linear," "center," "parallel," "perpendicular," "aligned," or particular measurements or other units as used herein can be approximate, need not be exact, and can include typical engineering tolerances. For example, a motion described as linear can be achieved with linkages that are actually creating curved motion.

Figure 1:
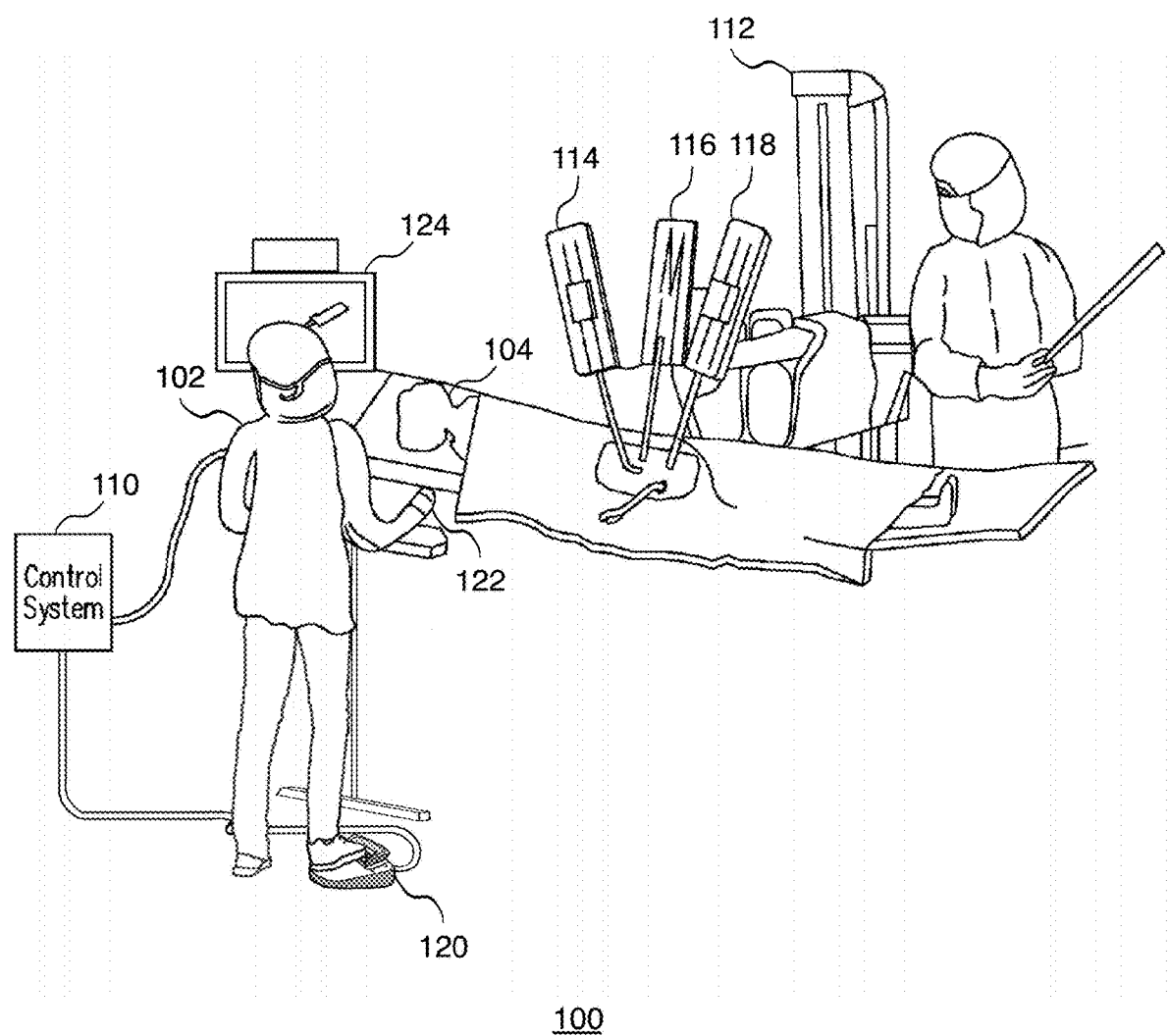
FIG. 1 is a diagrammatic view of an example surgical environment, according to some implementations.

FIG. 1 is a diagrammatic view of an example minimally invasive surgical environment 100, according to some implementations. As shown, environment 100 includes a surgeon 102 who is operating on a patient 104 who may be situated on an operating table (e.g., table, bed or other support). Surgeon 102 is operating a control system 110 that controls a teleoperated surgical system 112 (sometimes referred to as the cart) having teleoperated slave surgical instruments 114, 116, and 118.

In various implementations, surgeon 102 manipulates surgical instruments 114, 116, and 118 using a foot controller 120 and one or more hand controllers 122 (only one hand controller is shown in this example). In the example shown, foot controller 120 is a single-foot controller operated by a single foot of the user (surgeon 102). Implementations of foot controller 120 and hand controllers 122 are described in more detail below. In some implementations, surgeon 102 may view actions of surgical instruments 114, 116, and 118 on patient 104 via display 124.

In various implementations, control system 110 may be referred to as a master control workstation (e.g., surgeon's console or patient-side surgeon interface), and surgical instruments 114, 116, and 118 may include end effectors that are included in surgical tools, where the surgical tools are included in respective arm assemblies of a slave device.

Referring in general to FIG. 1, some implementations include a patient-side surgeon interface 110 that provides enhanced capabilities in using a minimally invasive, teleoperated surgical system 100. Unlike conventional teleoperated surgical systems, patient-side surgeon interface 110 may include one or more components within a sterile surgical field of the surgery. The sterile surgical field is a non-contaminant zone or space near the surgical site in which bacteria and other contaminants are reduced to reduce potential bacterial (or other) contamination to the surgical site during surgery. For example, the one or more components in the sterile field can include the hand controller(s) 122 and the foot controller 120. These components in combination with an image on display device 124 allows a surgeon 102 to control teleoperated surgical instruments 114, 116, and 118 from within the sterile surgical field. Thus, patient-side surgeon interface 110 permits a surgeon 102 to work within the sterile surgical field adjacent to a patient 104 undergoing surgery, e.g., using ungrounded master controllers (which are sterilized), so the surgeon operates the teleoperated device while at the patient's side in the surgical field.

Controlling (using control system 110) slave surgical instruments 114, 116, and 118 from within the sterile surgical field permits teleoperated surgery (e.g., minimally invasive surgery) combined with direct visualization of patient 104, the cart 112, any manually operated surgical instruments utilized directly with the surgeon's hand 122, and other machines and/or instruments being used in the surgery, etc., by surgeon 102. The proximity to patient 104 allows surgeon 102 to control one or more end effectors of teleoperated slave surgical instruments 114, 116, and 118 together with one or more manually controlled instruments, e.g., a laparoscopic instrument or a stapler.

A patient-side surgeon interface may be implemented with the surgeon in a standing position proximal the patient 104. Foot controller 120 provides sensor input to control system 110. In some implementations, the foot controller is coupled one or more processors, e.g., in control system 110 or other device of the system. In some implementations, the processors are configured to control and enable a slave device including surgical instruments to perform multiple functions. For example, the plurality of functions can include activating functions of the surgical instruments, switching user control between the surgical instruments, enabling and disabling user control of surgical instruments (e.g., a clutch function), and other functions of the slave device as described herein.

Figure 3:
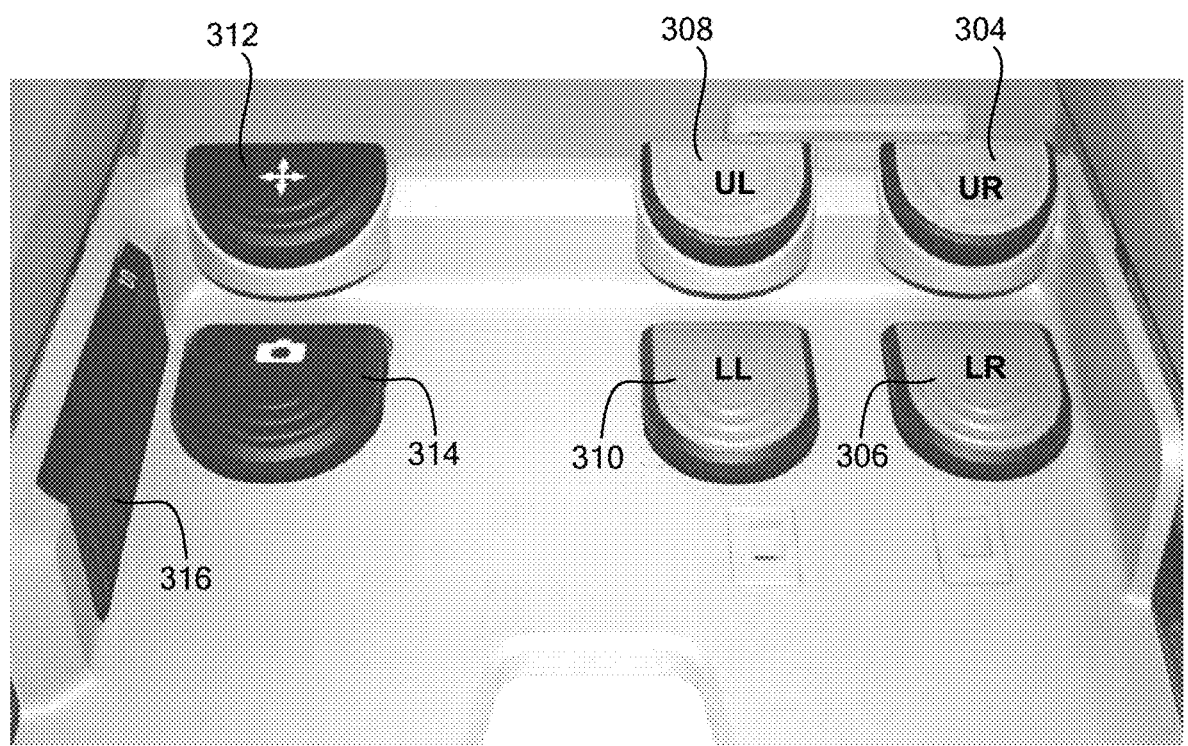
FIG. 3 is a top view of a controller for a seated user, according to some implementations.

In this example configuration, foot controller 120 is a standing foot control, operated by a non-weight-bearing (operating) foot of a standing user (e.g., surgeon 102). In various scenarios, the standing user can place some weight on the heel of the operating foot. For example, a surgeon may activate foot-activated functions using the foot controller 120 with one operating foot while standing. The use of single foot controller 120 may be preferable for a standing surgeon compared to using foot controllers operated with two feet (two-foot controllers) as often used with sitting surgeon consoles. For example, an implementation of a two-foot controller is shown in FIG. 3, showing an array of four foot switches (or pedals), which can be activated by a sitting user. Using such an array of four conventional foot switches may challenge a standing surgeon, due in part to the shifting of the surgeon's center of gravity to activate different switches with different feet. This shifting of the surgeon's center of gravity is additionally disadvantageous when the surgeon is operating master controllers in his or her hands, especially ungrounded master controllers, since this motion may cause unintentional motion of the master controllers. Furthermore, the one-foot controller 120 enables the surgeon to be more mobile in the operating room since the surgeon's non-active foot can be positioned more flexibly. In addition, a single-foot controller 120 can be made smaller in its size than a two-foot controller, which is advantageous in crowded operating environments. The smaller size can also allow the surgeon to be closer to the patient and/or any displays for performing an operation.

In other implementations, a foot controller 120 may be used by a sitting user, such as a surgeon or other operator in a chair, or a surgeon sitting and operating a workstation or surgeon console. For example, a surgeon may operate one or more foot controllers 120 while also operating grounded master hand controllers of the console. Other configurations can allow a user to use a foot controller 120 while standing at a workstation or console, e.g., while using grounded master hand controllers.

Various implementations of foot controller 120 may also provide additional advantages as described herein. For example, the foot controller 120 may be operable without having to lift the entire foot of the user. In contrast, having to select a foot switch to activate from four foot switches (e.g., as shown in FIG. 3) and having to raise a foot and move it to another foot switch may cause the user to look at his or her feet to perform this activation. This causes a surgeon using the foot switch to undesirably move his or her eyes from the surgical site, and in some configurations there may be difficulty in looking down or obstructions to seeing one's feet while positioned near the patient table. Another advantage of foot controller 120 is the smaller range of motion required by the user's foot. A smaller range of motion can reduce or eliminate strain on the foot. Also, using features described herein, multiple switches or other controls activatable by the foot may be used with less foot travel than may be required for the same number or fewer previous types of foot switches.

In some implementations, captured images can be transmitted to the viewer of a workstation and/or transmitted to one or more other displays, e.g., a display 124 coupled to a slave device 114, 116, or 118. For the purposes of this disclosure, "workstation" is defined as comprising one or more hand controllers (e.g., an ungrounded hand controller 602, 606 as shown in FIG. 6, grounded hand controllers, or other type of hand controllers), one or more foot controllers 120, a control system 110, and one or more displays 124. In some examples, a slave device may include arm assemblies (shown in FIG. 5, elements 514, 516, and 518), which may include a surgical tool. Each surgical tool can include a surgical end effector, e.g., for treating tissue of the patient.

In some implementations, the arm assemblies may be caused to move and articulate the surgical tools in response to manipulation of master controllers at the workstation by the user 102, so that the user 102 can direct surgical procedures at surgical sites, e.g., through minimally invasive surgical apertures. For example, one or more actuators coupled to the arm assemblies may output force to cause links or other portions of the arm assemblies to move in particular degrees of freedom in response to control signals received from the workstation. The workstation can be used within a room (e.g., an operating room) with the slave device, or can be positioned more remotely from the slave device (e.g., at a different location than the slave device).

Some implementations of the teleoperated system 100 can provide different modes of operation. In some examples, in a non-controlling mode (e.g., safe mode) of the teleoperated system 100, the controlled motion of the manipulator slave device is disconnected from the master controllers of the workstation in disconnected configuration, such that movement and other manipulation of the master controllers does not cause motion of the manipulator slave device. In a controlling mode of the teleoperated system (e.g., following mode), motion of the manipulator slave device can be controlled by the master controllers of the workstation such that movement and other manipulation of the master controllers causes motion of the manipulator slave device, e.g., during a surgical procedure.

Some implementations can include one or more components of a teleoperated medical system such as a da Vinci® Surgical System (e.g., a Model IS3000 or IS4000, marketed as the da Vinci® Si® or da Vinci® Xi® Surgical System), commercialized by Intuitive Surgical, Inc. of Sunnyvale, Calif. However, features disclosed herein may be implemented in various ways, including teleoperated and, if applicable, non-teleoperated (e.g., locally-controlled) implementations. Implementations on da Vinci® Surgical Systems are merely exemplary and are not to be considered as limiting the scope of the features disclosed herein. For example, different types of teleoperated systems having slave devices at worksites can make use of actuated controlled features described herein. Other, non-teleoperated systems can also use one or more described features, e.g., various types of control systems and devices, peripherals, etc.

In some implementations, a controlled slave manipulator device can be a virtual representation of a device, e.g., presented in a graphical training simulation provided by a computing device coupled to the teleoperated system 100. For example, a user can manipulate master hand controllers and/or foot controller(s) to control a displayed representation of an end effector in virtual space of the simulation, similarly as if the end effector were a physical object coupled to a physical slave device. Some implementations can use master hand controllers and foot controllers in training, e.g., demonstrate the use of instruments and controls of a workstation including controllers, pedals or foot switches, etc.

In various implementations, other types of computer-assisted teleoperated systems can be used with one or more foot controller features described herein, in addition to surgical systems. Such teleoperated systems can include controlled slave devices and slave instruments of various forms. For example, submersibles, bomb disposal units, industrial applications, applications in hostile environments and worksites (e.g., due to weather, temperature, pressure, radiation, or other conditions), general robotics applications, and/or remote-control applications (e.g., remote controlled vehicle or device with a first-person view), may utilize teleoperated systems that include slave devices for sensory transmission (conveyed visual, auditory, etc. experience), manipulation of work pieces or other physical tasks, etc., and may use mechanically grounded and/or ungrounded master controllers to remotely control the slave devices. Any such teleoperated systems can be used with the various foot controller features described herein.

In some implementations, non-teleoperated systems can also use one or more features of foot controllers as described herein. For example, various types of control systems and devices, peripherals, etc. can be used with foot controllers. In some examples, a manual laparoscopic device can be used by a surgeon or other operator standing next to a patient to perform surgical procedures on the patient without use of a teleoperated slave device, or in conjunction with use of a teleoperated slave device. Such an operator can use one or more foot controllers as described herein to control functions of one or more surgical instruments used in the manual procedures, e.g., irrigation, suction, cutting, lighting, camera, etc.

Figure 2A:
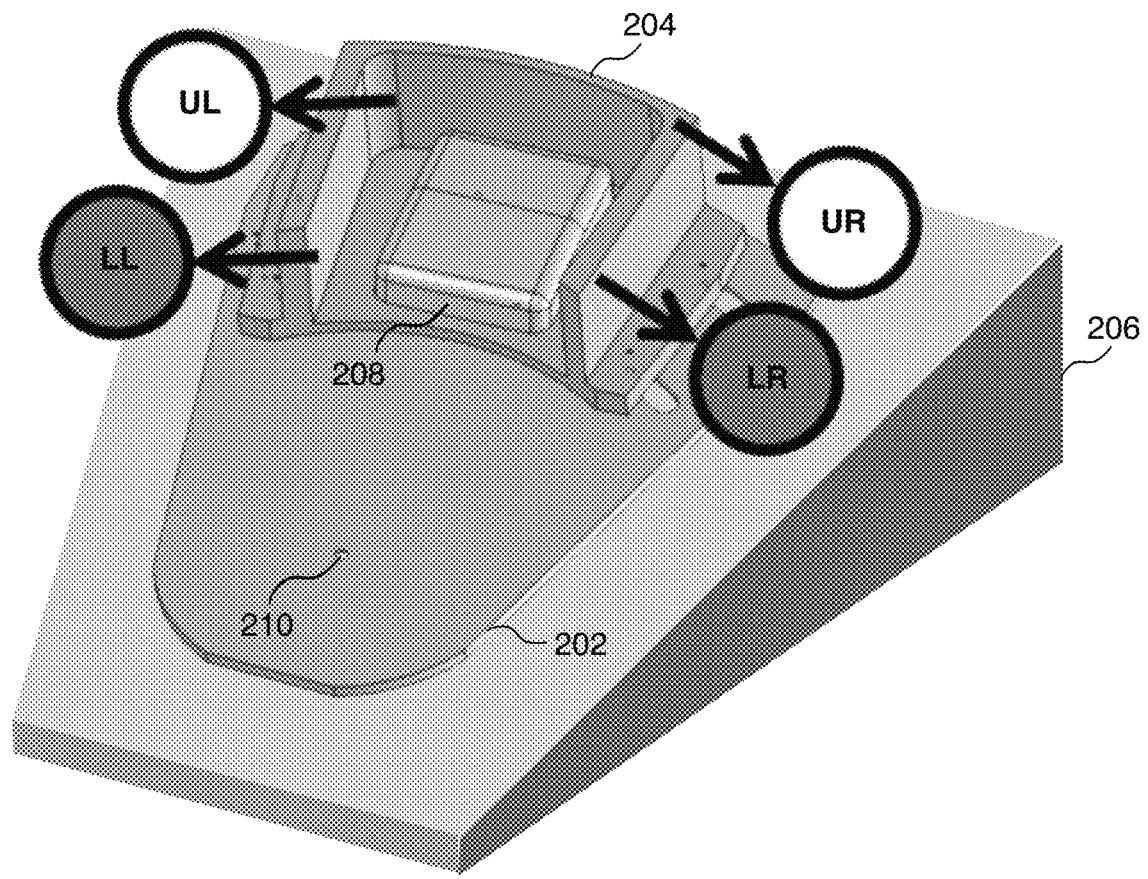
FIG. 2A is a perspective view of a foot controller, according to some implementations.

FIG. 2A is a perspective view of a foot controller 200 according to some implementations. For example, foot controller 200 may be a single-foot controller operable with a single foot of a user. In some implementations, foot controller 200 may be operable by a standing user, or may be used by a user alternately sitting and standing. Some implementations of foot controller 200 can be operated by a sitting user. Foot controller 200 may be used to implement foot controller 120 of FIG. 1. In various implementations, foot controller 120 is adapted to provide a small distance the user's foot needs to move to operate controller functions as described herein.

As shown, foot controller 200 includes a base member 202, a cradle member 204, and stationary portion 206. In some implementations, cradle member 204 may be positioned on and movably coupled to base member 202. Base member 202 may be positioned on and moveably coupled to stationary portion 206, e.g., the base member 202 is coupled between cradle member 204 and stationary portion 206. In some implementations, stationary portion 206 can rest on the ground, e.g., may be flat. In some implementations, as shown in FIGS. 2A through 2E, stationary portion is tilted, e.g., wedge shaped. Stationary portion 206 may be of different elevations, depending on the particular implementation. For example, stationary portion 206 may be tilted at a particular number of degrees, or may be substantially flat, depending on the particular implementation. In some implementations, stationary portion 206 may be connected to a chassis (not shown), e.g., a structure providing additional supports, members, etc.

Cradle member 204 is configured to receive a foot of a user. For example, referring to FIG. 1, foot controller 120 is receiving the right foot of surgeon 102. In FIG. 2A, also shown is an input control 208 and a pivot point 210, which are described in more detail herein. In some implementations, a user's heel can be positioned at or near point 210 during operation of the foot controller. In some implementations, an adjustable heel pocket or adjustable cradle member length and/or width can be employed to adjust for user foot sizes.

In some implementations, as shown, cradle member 204 is moveable with respect to base member 202 along a first one of a left-right axis (e.g., a left-right degree of freedom) of the foot controller and a forward-back axis (e.g., a forward-back degree of freedom) of the foot controller. In some implementations, the base member 202 (and thus cradle member 204) is moveable with respect to stationary portion 206 along a second (different) one of the left-right axis and the forward-back axis. For example, in the described implementation of FIGS. 2A-2E, cradle member 204 is moveable along the left-right axis with respect to base member 202, and base member 202 is moveable along the forward-back axis with respect to the stationary portion 206.

In various implementations, cradle member 204 is moveable to multiple positions along multiple paths, e.g., paths associated with respective multiple positions. In some implementations, the positions are predetermined positions within the degree(s) of freedom of the cradle member. In some implementations, the paths are predetermined paths within the working area or volume of movement of the cradle member 204. In some implementations, the cradle member 204 is constrained in its movement to the paths, e.g., to predetermined paths. In some implementations, the multiple positions are reached along the paths, e.g., each of multiple positions is reached by moving the cradle member along one (or alternatively, multiple) paths associated with that position.

In some implementations, one or more of the cradle paths have a component direction along the left-right axis (e.g., in the left-right degree of freedom), and one or more of the cradle paths have a component direction along the forward-back axis (e.g., in the forward-back degree of freedom). In some examples, a path may have a component direction along the left-right axis and not a component direction along the forward-back axis, such that it does not allow forward-back movement of the cradle member. A path may have a component direction along the forward-back axis and not a component direction along the left-right axis, such that it does not allow any left-right movement of the cradle member. A path may have a component direction along the left-right axis and a component direction along the forward-back axis, such that it allows movement of the cradle member along both the left-right axis and along the forward-back axis. The left-right axis movement and forward-back movement can be separate (e.g., in succession), and/or can be combined to allow diagonal paths and diagonal movement of the cradle member 204 within the cradle movement workspace. In some implementations, one or more of the paths have a direction along a left-right axis of the controller, a forward-back axis of the controller, or any combination thereof.

Figure 2B:
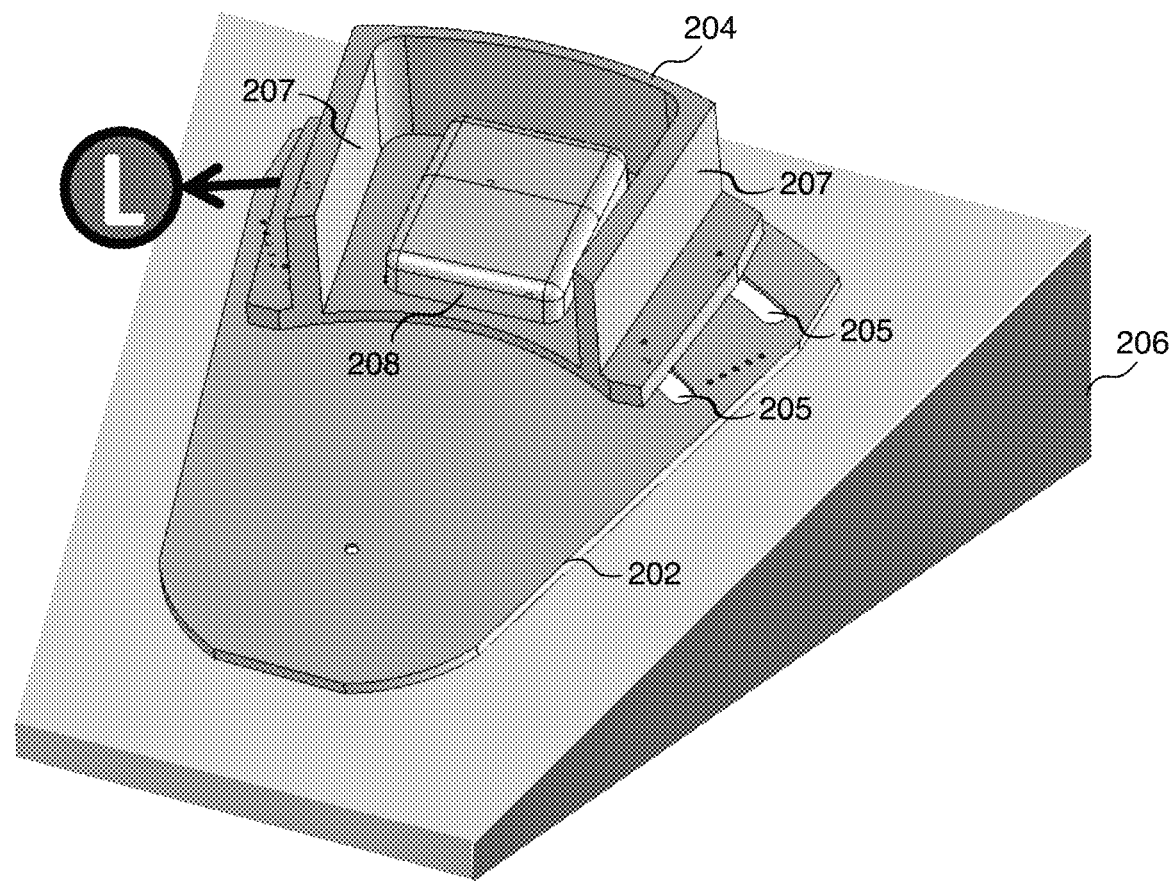
FIG. 2B is a perspective view of a foot controller with a cradle member in a left (L) position, according to some implementations.
Figure 2C:
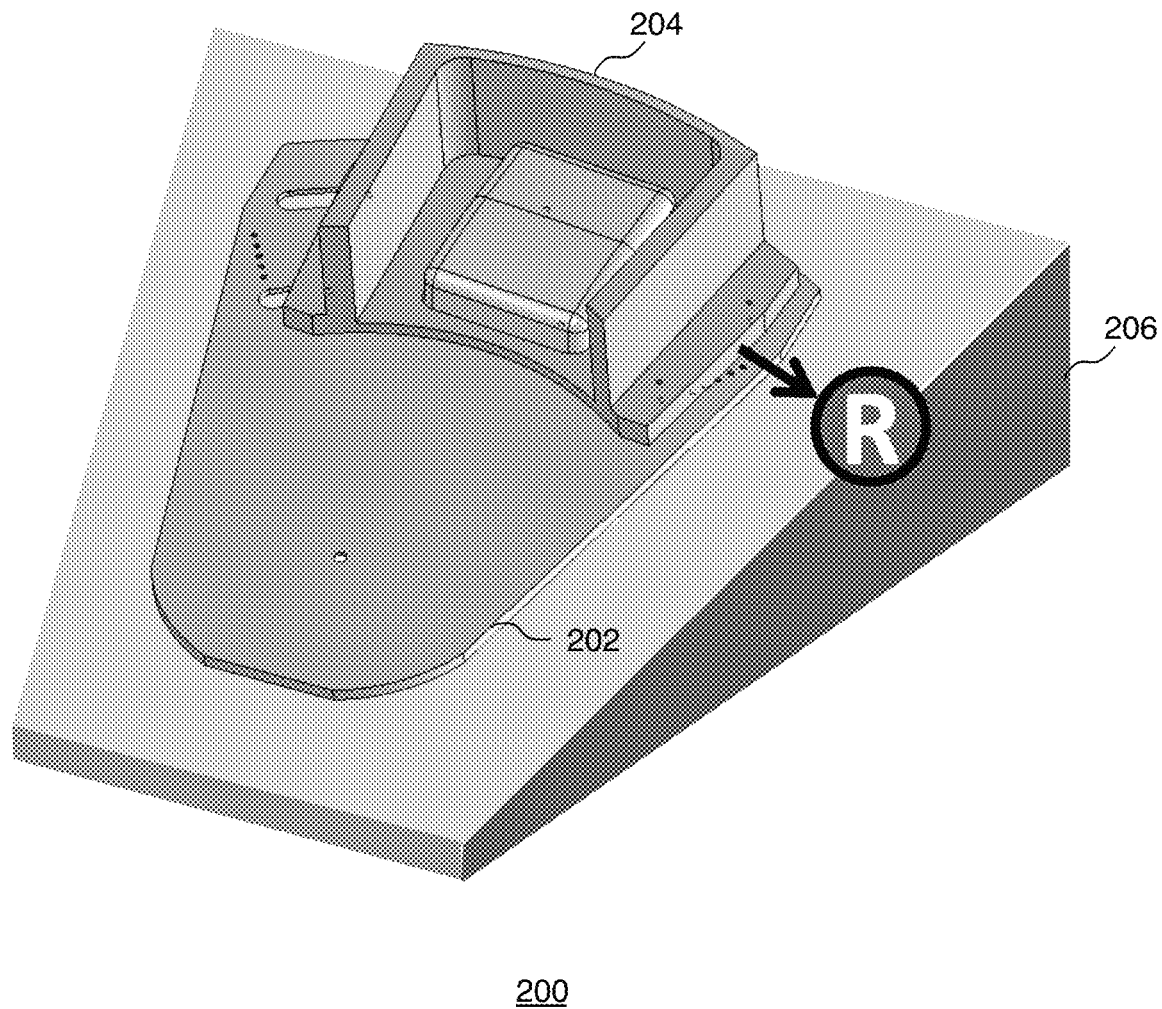
FIG. 2C is a perspective view of a foot controller with the cradle member in a right (R) position, according to some implementations.
Figure 2D:
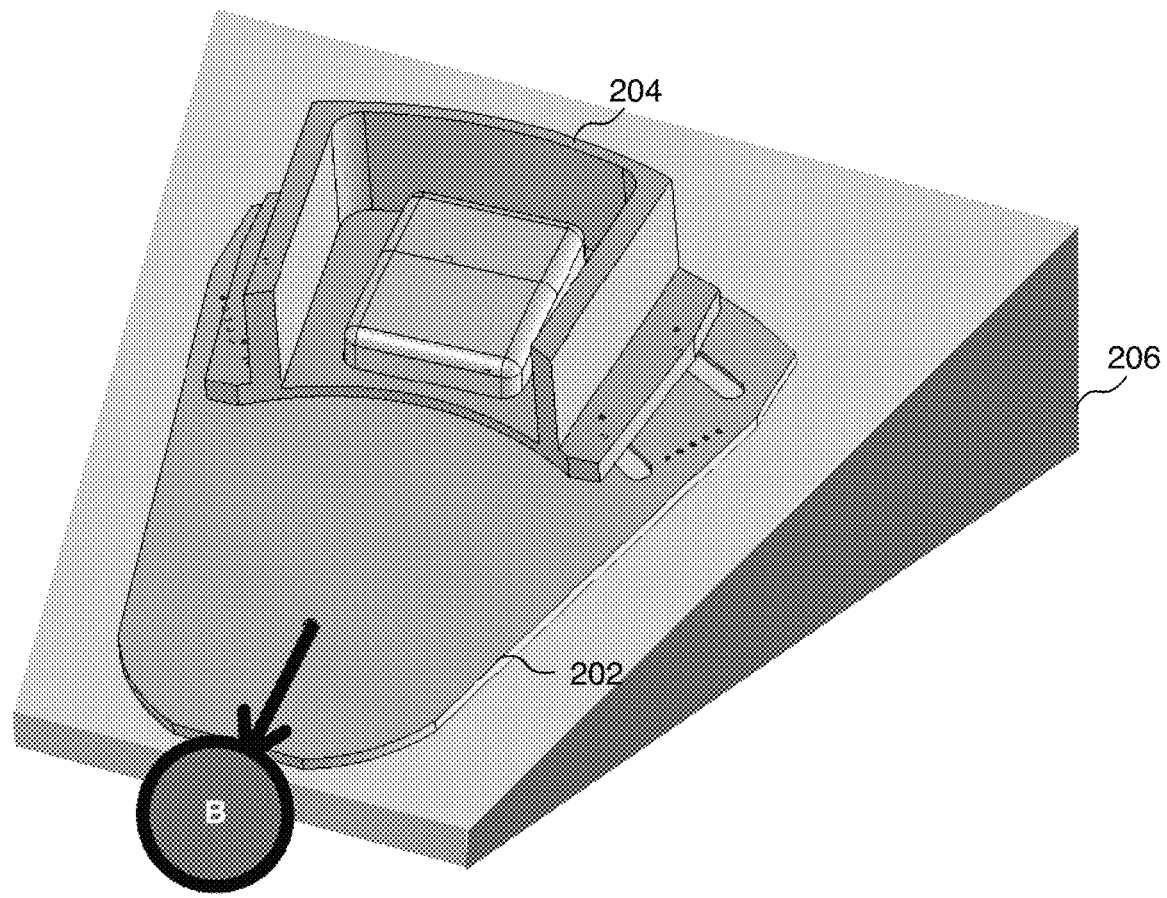
FIG. 2D is a perspective view of a foot controller with the cradle member in a back (B) position, according to some implementations.

In some examples, the multiple positions include a center position, a left position, a right position, a front position, and a back position. In some implementations, as shown in FIG. 2A, cradle member 204 may move to four positions (indicated by the arrows)—upper right (UR), lower right (LR), upper left (UL), and lower left (LL). In these examples, these four positions result from different combinations of possible positions of cradle member 204 on the left-right axis (e.g., left or right) and possible positions of the cradle member on the forward-back axis (e.g., forward or back). Thus, the upper right (UR) position results from cradle member 204 moving to the forward position on the forward-back axis and moving to the right position on the left-right axis, the lower right (LR) position results from cradle member 204 moving to the back position on the forward-back axis and moving to the right position on the left-right axis, and so on. For example, as shown in FIGS. 2B-2D, cradle member 204 can move approximately along a left-right axis (e.g., pivot about a point 210), and cradle member 204 and base member 202 can move as a unit along a forward-back axis. As described below, in some implementations, the foot controller 200 includes one or more guides coupled between cradle member 204 and base member 202, and/or between base member 202 and stationary portion 206. The guides limit movement of the cradle member to paths. For example, a guide can include one or more grooves (e.g., tracks or apertures) that guide the cradle member along predetermined paths.

In some examples, FIG. 2B illustrates a left (L) position and FIG. 2C illustrates a right (R) position of cradle member 204. In this example, cradle member 204 is movable to the left and right positions along a curved path approximately along a left-right axis, where the path is provided by a number of grooves 205 (e.g., tracks or apertures) provided in the base member 202. In this example, the cradle member 204 is not movable along the forward-back axis relative to the base member 202. A coupling can be used to movably couple cradle member 204 to base member 202. For example, one or more blocks or elements (not shown) can extend from the underside of cradle member 204 which are each aligned with and engage with a corresponding one of the grooves 205. In this example, two grooves 205 are shown, although other numbers of grooves can be used. The grooves 205 are traced in base member 202 to form the desired path for the cradle member along the left-right axis, such that cradle member 204 slides left and right guided by grooves 205. In this example, grooves 205 are curved such that cradle member 204 is positioned closer to the back of base member 202 at the furthest left and right positions and is positioned closest to the front of base member 202 at the middle of the path formed by grooves 205. This provides a pivoting movement of the cradle member 204 approximately about an axis, e.g., a pivot axis at a point 210 at a back end of the cradle member, to enable movement of the cradle member in a left-right axis, where the pivot axis is perpendicular to a plane of cradle movement.

In the examples of FIG. 2A-2E, the cradle member 204 is provided near the front of the foot mechanism 200 such that the cradle member can be moved laterally (left and right) by the front of the foot of the user while the heel of the foot contacts and pivots on base member 202. This configuration can provide stability to a standing user while moving the cradle member left and right. For example, in some cases, pivoting or rotating may encourage a user's heel to be more stationary, which may be advantageous to allow the use of hand master controllers to be more stable. Additionally, this pivoting of the foot about the heel is a natural motion that allows for a single input control 208 (described below) to be perceived by the user as two input controls that are placed side-by-side (e.g., one input control at a left position, the other input control at a right position).

In other implementations, grooves 205 can be linear to provide, for example, motion of the cradle member along the left-right axis as linear sliding (translation) rather than pivoting or rotating. In some implementations, grooves 205 can be curved in other ways than shown, e.g., to form cradle member paths having other routes or shapes. In some implementations, the grooves can be provided in cradle member 204 and one or more elements extending from base member 202 can engage the grooves. Other types of couplings or bearings can be used to movably couple cradle member 204 to the base member 202, some examples of which are described herein. Also, the pivot about point 210 can be implemented using a single-axis bearing or such, e.g., where cradle member 204 can hold the full length of the user's foot.

In some implementations, the cradle member 204 includes walls 207 on the left and right sides of the cradle member. The walls can be configured to receive a side of the user's foot when the cradle member is desired to be moved left or right at least partially along the left-right axis, and thereby assist such movement, and providing surfaces to move the cradle 204 without pressing on the cradle member and activating the input control 208.

Figure 2E:
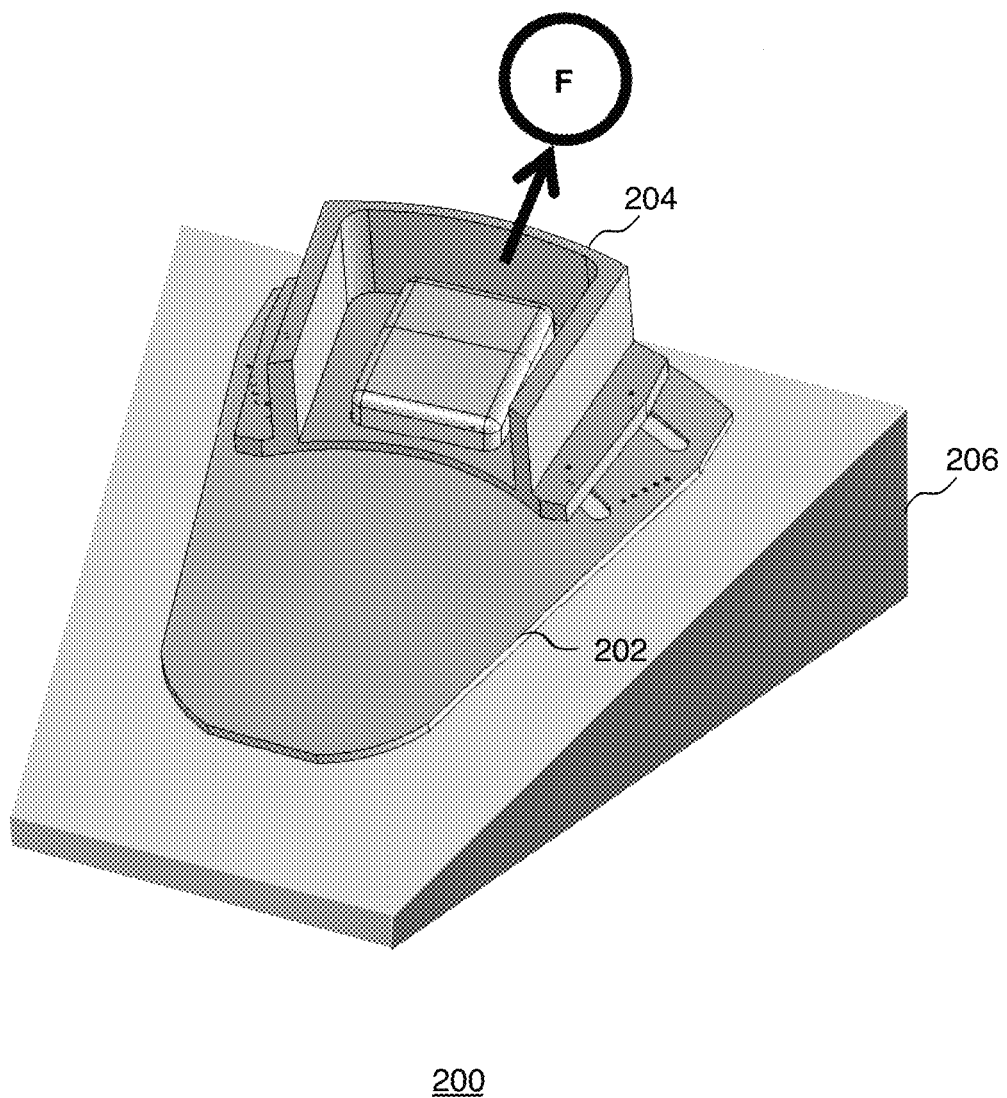
FIG. 2E is a perspective view of a foot controller with the cradle member in a forward (F) position, according to some implementations.

In further examples, FIG. 2D illustrates a back (B) position and FIG. 2E illustrates a forward (F) position of cradle member 204. In this example, cradle member 204 and base member 202 are movable in unison along a linear path along a forward-back axis relative to stationary portion 206. In some examples, a linear coupling can be used to couple base member 202 to stationary portion 206, which allows base member 202 to slide linearly with respect to stationary portion 206. For example, elements of the base member can engage with and be guided by grooves (e.g., tracks or apertures) in stationary portion 206, or vice-versa, similarly as described above. Other types of couplings or bearings can be used to movably couple base member 202 relative to stationary portion 206.

In some implementations, the foot controller can be operated with one foot, e.g., by a standing or sitting user. For example, to accommodate use by a single foot, the range of motion for the cradle member (e.g., along the left-right and forward-back axes) can be smaller than a range of foot motion needed to operate a corresponding two pedal system. In some implementations, the positions of the cradle member correspond to states of a two-foot pedal system. An example of a pedal system is illustrated in FIG. 3, which includes multiple pedals (foot switches) (including upper and lower pedals) operated by two feet. In some implementations, the left (L) positions of the cradle member 204 can correspond to the left (L) pedal(s) of a four-pedal system, and the right (R) positions of the cradle member 204 can correspond to the right (R) pedal(s) of a four-pedal system. Referring to the example of FIG. 3, the forward (upper, U) positions of the cradle member 204 can correspond to the upper (U) pedal(s) 304 and 308 of the pedal system, and the back (lower, L) positions of the cradle member 204 can correspond to the lower (L) pedal(s) 306 and 310 of the pedal system.

In some implementations, cradle member 204 may move to more than four positions. For example, the cradle member can be positioned in a center position. In some examples, the center position can be positioned at the center of the forward-back axis and the center of the left-right axis. Other positions can include intermediary positions provided in the paths along the left-right axis and/or the forward-back axis. Other positions can include positions provided in additional or different paths of the cradle member 204, e.g., diagonal paths having component directions along both the left-right axis and the forward-back axis, etc.

In some implementations, cradle member 204 can be physically biased toward a center position of cradle member 204 (e.g., a position at or near the center of the left-right axis and/or the forward-back axis). In some implementations, the physical bias (e.g., restoration force) can be provided using a passive element, e.g., a spring that is connected between cradle member 204 and base member 202, and/or connected between base member 202 and stationary portion 206. If the cradle member is moved away from the center position, the spring biases the cradle member to move to the center position. Other types of mechanisms or elements can be used to provide a restoration force to the cradle member. For example, one or more cam mechanisms can be used to provide a restoring force, as described with reference to FIGS. 8 and 9. In some implementations, active actuators (for example, motors), other types of passive actuators to provide braking, damping, or friction forces, etc. can be used to provide a restoring force.

In some alternate implementations, cradle member 204 can be made moveable (e.g., linearly) along the forward-back axis relative to the base member 202, and base member 202 can be made moveable left and right to move both base member 202 and cradle member 204 along the left-right axis. Such movement of base member 202 can be linear (e.g., in linear grooves), or can be rotation or pivoting around a pivot point, e.g., pivot point 210 (e.g., a location or point receiving the heel of the user's foot) approximately along the left-right axis. For example, base member 202 can be configured to pivot about a pivot axis at a back end of the cradle member to enable movement of the cradle member in a left-right axis, where the pivot axis is perpendicular to a plane of cradle member movement. Some examples are described below for FIGS. 13-16. In other implementations, additional movement or degrees of freedom can be provided to cradle member 204 and sensed for function activation similarly to the described movement. For example, movement can be provided along a vertical axis (e.g., z-axis) perpendicular to the surface of stationary portion 206 or the ground, and/or in additional directions or combinations of directions in the plane parallel to the surface of stationary portion 206 or the ground.

In some implementations, particular configurations of grooves may be used in order to assist in guiding the user to distinct cradle member positions. In one example, trident-shaped grooves can be used, as described below with respect to FIG. 10, to guide the cradle member along particular paths such as left-forward, right-forward, or other combinations of directions. Additional cradle member positions can also be provided in the grooves, e.g., at junctions of component paths. For example, there may be a distinct cradle member position at the bottom of each trident "elbow" where the left-right path meets the forward-back path. Other locations can also be used to provide different control functions.

In some implementations, an elevation of one or more paths of the cradle member can vary at different positions of the cradle member along the path. The elevation can be in a direction perpendicular to a plane defined by the left-right axis and the forward-back axis, or a plane defined by the ground. For example, the varying elevation can provide a varying elevational slope of travel to the cradle member. Such varying elevation can be provided using a sloped surface of stationary portion 206 and/or of base member 202. In some examples, the varying elevation can be provided as a low elevation at the back of the foot controller, and a gradual increase in elevation toward the front of the foot controller, like a ramp. The surface of stationary portion 206 shows such an example in FIGS. 2A-2E. In another example, the elevation can vary in the opposite way, e.g., a higher elevation at the back of the foot controller, gradually falling to a lower elevation at the front of the foot controller. In another example, elevation can be varied along a left-right axis of the foot controller. For example, elevation can be lower at the left side of the controller, rise gradually to a highest elevation in a direction toward a center position in the left-right travel of the cradle member 204, and fall gradually from the center position towards the right side of the foot controller. For example, this can cause a bias toward left or right positions of the cradle member as provided by gravity. A combination of two or more of these varying elevations can be used in some implementations. In another example, the base member can include a convex top surface, and the cradle member tilts while moving laterally or longitudinally across the convex top surface of the base member.

In additional examples of a varied tilt angle of the cradle member, an end or edge of the cradle member (and/or base member) can be caused to tilt up (e.g., its front end moving upward, a greater distance from the ground, more than its back end) as the cradle member is moved in a particular direction or degree of freedom.

Tilting components of the foot controller may benefit user ergonomics, e.g., to tilt up the foot at a forward position and cause the foot to be more level at a back position. Additionally, a tilting foot cradle may provide more proprioception as to the location of the cradle member, for example in the left/right and forward/back degrees of freedom. In some examples, two wheels at a side of the cradle member can be rolled on a curved surface in the direction of cradle member travel, where the curved surface has different slopes to cause the tilt. In some implementations, the cradle member can tilt for left and right movement. For example, the left side of the cradle member can tilt higher than the right side when moving to the left past the center position, and similarly the right side can tilt higher than the left side when moving to the right past the center position. In some implementations, a pivot bearing (e.g., at the heel) can accommodate the tilting, e.g., by providing added clearance in a rotary bearing, using a coupling that is a ball, using a flexure coupled between tilting and non-tilting components to allow the tilting movement, etc. In some implementations, a tilting feature can also bias the cradle member to a certain position, for example the center position, e.g., using gravity and/or the force from the user's foot caused from an inclined surface. In additional examples, an outer edge of the cradle member (and/or base member) can lift up as it is moved, causing a tilt to the cradle member (and/or base member); or the outer edge can drop down during such movement. In some implementations, such tilt can increase the further the cradle member is moved, e.g., from a particular position such as the center position.

In various implementations, foot controller 200 also includes one or more sensors that are operative to sense that the cradle member is located at a particular position of the available positions. Some examples of sensors are described below with respect to FIGS. 7-13. A sensor can output a sensor signal indicative of that the cradle member 204 has been sensed at a particular position. In some examples, the sensor signal can cause activation of a particular function provided by a system in communication with the sensor and associated with the particular position at which the cradle member has been sensed.

In some implementations, foot controller 200 can also include one or more input controls, e.g., input control 208 (also referred to as an "activation control," "activation control switch," or "activation control button"). In some examples, input control 208 is a physical button or switch that is operative to be activated by user input, e.g., engaged or pressed downward by at least a portion of the foot of the user that is operating the foot controller 200. For example, in FIG. 2B, the cradle member 204 and input control 208 is provided near the front of the foot controller 200 such that the input control can be activated by the front of the foot of the user. The activation of input control 208 causes a control signal (e.g., a button signal) to be output by the input control, e.g., to a controller or system. The controller can be in the housing of the foot controller or in a separate device in communication with the foot controller. In some examples, the control signal can cause activation of a particular function provided by a system in communication with the input control. In some implementations, the control signal is associated with one or more functions that are activated in response to receiving the control signal regardless of the position of the cradle member at the time that the input control was activated. In some implementations, the control signal can cause activation of a particular function that is associated with the control signal and with the particular predetermined position of the cradle member when the control signal is sensed. Various other types of input controls can be also or alternatively be used to enable user activation of a control signal, e.g., optical sensors, capacitive sensors, pressure sensors, etc.

In some implementations, the foot controller can include one or more presence sensors that detect that a user's foot has been placed on or in cradle member 704. For example, optical sensors, pressure sensors, etc. can be used. Such sensors can be used in addition to input control 208. For example, the presence sensors can be used to determine whether a user is operating the foot controller, while the input control 208 can be used to sense activation of particular system functions by the user.

In some implementations, haptic feedback can be provided in the paths of cradle member 704. In some implementations, one or more of the paths can include one or more physical features, which provide a force effect to the cradle when the cradle is moved in the path. In some examples, the physical feature(s) can be provided in grooves in the cradle member 204, base member 202, and/or stationary portion 206 that provide cradle member paths. For example, a plurality of physical detents and/or a plurality of physical bumps can be provided in grooves 205 or other grooves used in forward-back movement.

Some implementations can provide haptic feedback using a haptic mechanism including one or more actuators (e.g., active motors, passive actuators or resistance elements, etc.). The actuator(s) can be directly or indirectly coupled to the cradle member and/or base member and can be commanded by the system to selectively output force on the cradle member along paths, e.g., to provide haptic feedback to a user when using the cradle member. Some examples of actuators are described below with respect to FIGS. 7-16.

In some examples, one or more actuators can provide resistive force to movement of the cradle member in one or more of the paths. In some implementations, the resistive force can be varied based on a control signal provided to an actuator from a controller. In additional examples, the actuators can, in conjunction with grooves or without the use of grooves, bias and/or guide the cradle member along the paths. For example, in various implementations, a restorative force to the center position is provided by an active actuator, a passive actuator, and/or a spring. In some implementations, the cradle member can include a power assist mechanism using one or more actuators to provide assistive force to the cradle member and assist the user when moving the cradle member between positions. For example, the assistive force can assist moving the cradle member through a directional change in a path by outputting a force in the changed direction toward a position at the end of the path. In one example, after the cradle member is moved forward along a forward-right path, an actuator can be controlled to output a force to the right to assist moving the cradle to the right along the remainder of the path toward the desired position.

In some implementations, one or more actuators coupled to the cradle member may output different haptic feedback, e.g., a different force effect, in each of two or more paths. A particular path or position can be associated with a particular force effect, where different paths or positions are associated with different force effects. For example, different force effects can be output by actuators onto the cradle member when the cradle member is moving or positioned in different paths. This can inform the user via feel as to which path (or part of a path) on which the cradle member is currently moving or positioned. In some examples, a higher-frequency vibration can be output on the cradle member when the cradle member is moved left or right, and a lower-frequency vibration can be output on the cradle member when moving forward or back. In another example, higher resistance to cradle member movement can be output in particular paths that are more important or cause more serious effects for a surgical procedure (e.g., paths that provide energy functions to a cutting tool or other surgical instrument that can cut tissue). Other force effects that can be output in particular paths can include one or more detents or bumps at different spacings, spring forces, texture (e.g., rough, non-smooth feel), etc. In some implementations, a damping force can be provided, e.g., causing the cradle member to feel as if moving through molasses.

Additional benefits of the use of actuators may include informing or reminding the user of context or states of the foot controller and/or of the controlled slave system. In some implementations, actuator(s) may be used to limit the positions available in a context-sensitive way. Such context can include the type of slave instrument controlled, the current state of the instrument, etc. For example, the actuators can allow movement of the cradle member to certain positions only when a function associated with that position is available. For example, some slave surgical instruments have energy A and energy B functions, and some instruments have only energy A, or no energy output at all. In this latter case, the actuators can be controlled by a control system to output force to block movement of the cradle to one or more positions associated with energy functions. Or, access to a certain cradle position can be allowed only when that function is available, or the actuator can output force to vibrate or push the cradle member out of a disallowed position.

In some implementations, additional structure can be provided for the foot controller 200. For example, a member or surface can be provided above the cradle member, e.g., attached to stationary portion 206. The surface can retain the user's foot in cradle member 204 by blocking upward movement of a foot out of the cradle member 204. For example, in some implementations, the cradle member can include a bicycle pedal-style cage or frame with a top surface covering at least a portion of the user's foot, allowing the user to position the foot in the cage. In some implementations, a second input control can be coupled to the surface above the cradle member and is available for user activation. For example, the second input control can be a button or other input control that faces the cradled foot of the user and is activated by being pressed upward by the top of the foot. For example, the second input control can be positioned in the opposite orientation to first input control 208 on the cradle member, e.g., upside-down relative to the first input control 208. In some implementations, one or more additional input controls can be provided on cradle member 204 which can be activated by the user moving the foot laterally within the cradle member 204.

In some implementations, the foot controller (or a second foot controller) can include a second cradle member operative to receive a second foot of the user. For example, the stationary portion 206 can be wider to allow room to place a second base member on the stationary portion 206, e.g., to the left or to the right of the base member 202. A second cradle member can be coupled to the second base member, to provide additional functions operated by the second foot of the user similarly to the cradle member 204 described above. Some implementations can activate particular functions associated with a combination of particular positions of both cradle members and/or activation of both input controls on the two cradle members.

FIG. 3 is a top view of a pedal controller 300 for a seated user, according to some implementations. Pedal controller 300 is one example implementation in which two feet of the user can be used to control various pedal switches.

On the right side of the controller 300, four pedals 304, 306, 308, and 310 can be activated by being pressed by a foot of a user, e.g., a right foot. The foot-switches 304, 306, 308, and 310 can be activated with one foot when the user is seated, where the foot can be moved by the user to the four different switches. In other configurations, pedals 304, 306, 308, and 310 can be positioned on a left side of the controller 300, or pedals 308 and 310 can be pressed by the left foot and pedals 304 and 306 can be pressed by the right foot. As shown, the four pedals 304, 306, 308, and 310 correspond to positions UR, LR, UL, and LL of FIG. 2.

In this example, on the left side of the controller 300, two pedals 312 and 314 can be activated by being pressed by a foot of a user, e.g., a left foot. The foot-switches 312 and 314 can be activated with one foot when the user is seated. In other configurations, pedals 312 and 314 can be positioned on the right side of the controller 300. As shown, the two pedals 312 and 314 correspond to particular functions of the controlled slave device, e.g., a master clutch control for pedal 312 and a camera control and focus control for pedal 314.

To the left of pedals 312 and 314, a pedal 316 can be activated by being pressed in the left direction by the side of the foot of the user. For example, pedal 316 can control an arm swap function of the slave device to switch control of the master controller to a different arm of the slave device. In some implementations, one or more functions of pedals 312, 314, and 316 can be included in different cradle member positions of the cradle members described herein.

Figure 4:
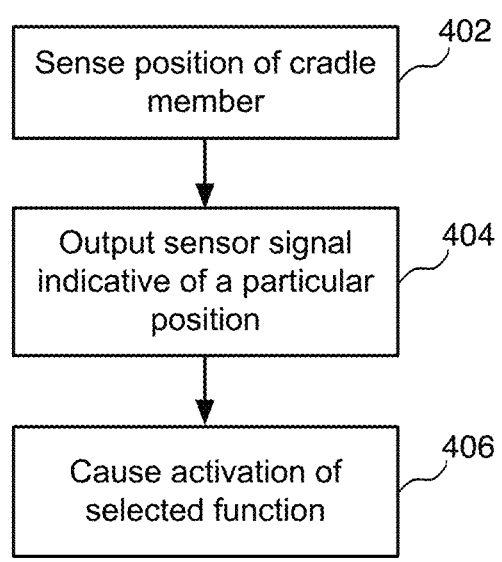
FIG. 4 is a flow diagram illustrating an example method for employing a foot controller according to some implementations.

FIG. 4 is a flow diagram illustrating an example method for employing a foot controller, according to some implementations. In block 402, the position of a cradle member of a foot controller is sensed. In some implementations, the cradle member is configured to receive a foot of a user, and is moveable by the foot of the user. In some implementations, the cradle member is operative to move to a plurality of positions. For example, the positions can include a center position, a left position, a right position, a front position, and a back position. Other positions can be provided in some implementations. The cradle member position can be sensed by one or more sensors of the foot controller as described herein.

In some implementations, an activation of one or more input controls of the foot controller may also or alternatively be sensed in block 402 (or before or after block 402), e.g., the pressing of a button or switch, or other activation of a control by the foot of the user of the foot controller.

In block 404, the one or more sensors output one or more sensor signals which are indicative of the particular position of the cradle member sensed in block 402. For example, the sensor(s) that detected the position of the cradle member in block 402 can output sensor signals to a control module or other system component (e.g., see FIG. 17). In some implementations, such a control module can be included in the foot controller. In some implementations, a control module can be also or alternatively provided externally to the foot controller, e.g., in a console, processor unit, slave device, or other device.

In block 406, the sensor signal causes activation of one or more selected functions of a plurality of functions provided by a system in communication with the sensor. The selected function(s) are based on the sensor signal indicative of the particular position at which the cradle member is sensed. For example, the control module can send commands to other system components to activate one or more functions based on the sensor signals.

The term "function" as used herein can include one or more actions or outputs of a controlled system (including operations or motions). For example, a function can include one instrument action or multiple instrument actions (e.g., actions performed serially and/or at least partially in parallel). In some implementations, a function can be a category of actions performed by a slave device or an instrument, e.g., a surgical instrument. In some examples, a cutting tool such as a knife or a surgical scissors may perform various actions in the category of cutting. In some implementations, the input control activating a function causes one or more actions associated with the activated function to be performed. For example, a cutting function can include one or more actions such as moving a scalpel to create an incision in a surgical site with a straight cut. Alternatively, the cutting function can include actions such as snipping a blood vessel with a surgical scissors, to be cauterized.

Selected functions can include any of a variety of functions of the system to which the foot controller provides input. For example, for a teleoperated medical device, a surgical slave device may include surgical instruments as described above. The surgical tools may include cutting tools, grasping tools, cauterizing tools, irrigation tools, suction tools, absorbing tools, etc. Various functions can be associated with such instruments or tools, including irrigation (injecting a liquid into or onto a surgical site or other location), suction (removing of such liquid), clutch (disengage control of slave device manipulator arms, e.g., to allow master controllers to be repositioned without such control), swapping control of a hand master controller between two instrument arms, camera functions (such as turning on or off a camera, zooming and rotating a video display provided by the camera, capturing or recording a scene at a physical location such as a surgical site, switching views provided multiple cameras, etc.), outputting energy by a cutting tool to cut or seal biological tissue, cut or coagulate tissue of a surgical site via energy, graspers, etc. In some implementations, the foot controller outputs teleoperation control signals based on the sensor signals to control functions including movements of a teleoperated device in communication with the foot controller.

In some examples, the cradle member can be positioned at a particular position of multiple activation positions in the degrees of freedom of the cradle member. The activation positions can include four positions as described above, and/or other positions. In some implementations, the center position of the cradle member can be an activation position. One or more of the positions, or each position, can correspond to a particular function or a different function. In some implementations, each position can be associated with a different function. As described herein, in some implementations, the cradle member is operative to return to a position corresponding to a neutral function in the absence of user input (e.g., user input force opposing such return).

An activated function can be a safe function or unsafe function. In this example, an unsafe function is a surgical function that has a higher risk or likelihood of being dangerous, e.g., able to cause injury to a patient, operator, or user. For example, such potentially dangerous functions can include controlling output of energy by a surgical instrument or performing another function of a surgical instrument having high-energy output, e.g., a cautery instrument. Examples of safe functions may include functions having less likelihood of such danger, e.g., clutch functions (which allow the user to disengage control of the teleoperated device, allowing free movement of master control handles or grips), switch instrument functions (allowing to change which manipulator arm is controlled by a master controller), timer functions, and other instrument functions such as camera functions. In an example scenario, some functions or movements may be unsafe to varying degrees. For example, a camera control may move a camera tip inside a body. While a camera tip is blunt and safer compared to scissors, the camera tip still imparts energy in the patient's body. Riskier functions may be required to be accessed using more deliberate motion(s) of the cradle member.

In some implementations, the functions activated by the foot controller can include primary functions and secondary functions. In some implementations, positions may correspond to yellow and blue pedals, which are associated to an industry standard code defining the primary and secondary functions (e.g., yellow foot switches 304 and 308 and blue foot switches 306 and 310 of FIG. 3). Examples of primary functions can include utilizing a cutting tool, a cauterizing tool, and a hemostat tool, and examples of secondary functions include support functions for the primary functions, such as camera control, clutch functions, directional functions, etc. For example, directional functions may include up movements, down movements, left movements, right movements of surgery tools. Other examples of primary functions and secondary functions may include cut (primary) and coagulate (secondary) (e.g., using energy to heat living tissue, where proteins coagulate and seal blood vessels). In some implementations, to coagulate, the surgeon grabs tissue and activates the input control long enough to get a seal as determined by the surgeon. Other examples of primary functions and secondary functions may include sealing (primary) and cutting (secondary). For sealing, the surgeon can use a vessel sealer instrument, e.g., a blade that travels through a vessel to be sealed, and apply energy to join tissues together. Specific algorithms may be used for sealing, such as an auto-timed and/or auto-operating sequence. Alternatively, a stapler function may used, which does not apply thermal energy to the site. Other examples of primary functions and secondary functions may include suction of blood and cleansing solution (primary) versus irrigation (secondary) with cleansing saline solution.

In some implementations, the input control 208 may be activated by the user (e.g., button pressed) to provide a control signal to activate a function associated with a current position of the cradle member, and/or activate a particular function independent of current cradle position. Some implementations can activate a function associated with the current position of the cradle member if the control signal is provided continuously (e.g., a button is continued to be pressed) for a time period over a threshold amount of time. For example, the control signal may command a neutral or default function to be activated irrespective of the cradle member position sensor signal if user input causes the input control to be continually activated for less than the threshold amount of time while the cradle member is positioned at the particular position corresponding to the function. For example, this can allow a surgeon to retract a mistakenly pressed activation button at the wrong position, e.g., if the button were released quickly. In some implementations, the threshold amount of time can be applied to particular non-time-sensitive functions. For example, the threshold amount of time can be omitted from a function of applying pressure to a surgical location quickly to stop blood flow, which can be activated immediately when the input control button is pressed by the user regardless of the threshold period of time.

In some implementations, the input control is operative to maintain output of the control signal to the system while the input control continues to be activated based on continued user input at the cradle member's particular position (e.g., a button is required to continue to be pressed in order to maintain output of the control signal to the system). In some implementations, the maintained output of the control signal causes the selected function to continue being activated by the system. For example, electrical energy may be applied to perform a coagulate function while the input control pedal or button is pressed. In some implementations, an audio signal may be output by the control system to indicate the energy is being applied. In another example, a clutch function may be activated when the input control may be activated as follows: the input control button is pressed and maintained in pressed state to activate the clutch function (enter non-controlling mode), hand master controls can be moved independent of manipulator arms, and the input control is deactivated by releasing the button with the foot when ready to go back into controlling mode. In another example, camera control may be activated as follows: the input control button is continually pressed to cause a hand controller to control camera position and/or orientation, and the button is released (deactivated) to return the hand controller back to controlling the position and grip of the instrument and not control the camera position and orientation.

In some implementations, an input control on the foot controller can be used as a toggle to enter or exit control modes. For example, an input control button is pressed and released once to enter camera mode, and is again pressed and released to return to instrument control mode. In another example, the input control can be used to toggle (swap or switch) the arm or instrument being controlled by a hand controller, e.g., switch control to a different manipulator arm on a slave device. In some implementations, an input control may be used to deselect and/or deactivate a function, e.g., using a deselect toggle. For example, an input control can maintain output of the control signal to the system once the input control has been activated (and released) based on user input at the particular position, causing the selected function to continue being activated by the system, until the input control is activated again by the user to deactivate the function. In some implementations, the input control can be used as a trigger to initiate a sequence of functions or actions, e.g., a staple sequence of a stapler instrument.

In some implementations, sensors of the foot controller, and/or a system connected to the foot controller, may distinguish or detect paths of the cradle member 204, or directions of cradle member travel on those paths, to activate or control different functions provided by the connected system. The different functions can be activated based on cradle member movement alone, or in combination with input control activation. In some examples, a cradle path can include multiple separate component paths, e.g., a first component path and a separate second component path. The multiple component paths can be provided in succession or one or more serial orders. In some examples, one component path can be a left or right path, e.g., along the left-right axis, and another component path can be a forward or back path, e.g., along the forward-back axis. For example, a predetermined path can be designated as forward-then-left, or left-then-forward, where the cradle member can be constrained to these directions in some implementations. In some implementations, one or more of the paths have a direction along a left-right axis of the controller, a forward-back axis of the controller, or any combination thereof (e.g., diagonally).

The order and/or direction of travel along component paths and/or degrees of freedom can be different, and different orders of and/or directions along one or more component paths can be associated with (e.g., designated to activate) different functions. For example, a first order or direction in which the cradle is moved through first and second component paths can determine a first function associated with the order, and a second order can determine a second, different function. In one example, an order of moving the cradle member 204 through a first component path (e.g., left) followed by a second component path (e.g., forward) can activate a first function of a system (e.g., an irrigation function), and an order of moving the cradle back through the second component path (back) followed by the first component path (right) can activate a second function that is different than the first function (e.g., a clutch function). In some implementations, two or more paths may be available to the cradle member to reach an activation position, and each path can be associated with a different function. For example, a left-then-forward path to a particular position may activate a first function, while a forward-then-left path to that particular position may activate a second function.

In some implementations the cradle member is operative to return to a default position (e.g., center position) after a user activates the input control. For example, a restoring force can be applied to the cradle member after activation of the input control, e.g., mechanically or using one or more actuators. In some implementations, the cradle member is operative to return to a default position while the selected function continues to be activated, until the input control is activated again to deactivate the function. In some implementations requiring the input control to continue to be activated in order to maintain output of the control signal to the system, the cradle member returns to the default position and the selected function is deactivated once the input control is no longer activated. In some implementations, the cradle member returns to a default position after a user presses the input control as a deselect toggle, which also deactivates the controlled function.

In some implementations, haptic feedback can be provided on the cradle member 204 and/or the input control 208, as described herein. For example, haptic feedback can be controlled by a control module (e.g., one or more processors) that controls the output of forces by one or more actuators. In some implementations of method 400 using actuators, for example, output of force by one or more actuators can be caused or provided in response to actuator control signals being received from the control module. The output of force can be performed after the output of the sensor signal(s) indicative of a particular position of the cradle member in block 404, where the magnitude and/or direction of force on the cradle member can be at least partially based on the sensed particular position. The force can also be based on activation status of one or more input controls 208. For example, a force can be output in response to activation of an input control.

In some implementations, a user interface (UI) and/or status readout can be displayed on one or more display devices of the system (e.g., display screens, virtual reality or augmented reality headsets or goggles, etc.). The user interface can display information related to operation of the foot controller. For example, the user interface can display one or more paths available for the cradle member. In some implementations, the user interface can display an indication of an activation position and an associated function to be activated by that position, and can display the path of the cradle member to reach that position from a current position of the cradle member (e.g., a center or neutral position of the cradle member). In some examples, the path can be displayed highlighted, e.g., showing arrows for movement direction on the path, flashing or blinking, etc. In some implementations, one or more sensor signals received from sensors of the foot controller cause a display device of the system to output a visual indication indicating at which position of multiple activation positions the cradle mechanism is currently positioned. For example, a processor of the system can command the display in response to receiving the sensor signals.

In some implementations, output such as haptic feedback and/or visual displays on a display device can be provided by the system to assist user operation of the foot controller. For example, a user interface may display warnings and/or error feedback on a display device, and/or audio output can be provided to indicates such warnings or errors. Such feedback can indicate functions that are potentially dangerous to a patient, and/or that a function to be activated is not appropriate (e.g., according to steps of a stored predetermined procedure) based on previous cradle member movement or previous function(s) activated. With haptic feedback, the system can output warning forces to the cradle member (e.g., a vibrotactile pulse, blocking a path, etc.) to notify the user. In some implementations, blocking or resistance forces can be controlled with one or more actuators to prevent or reduce the cradle member being moved into or out of a position. For example, if a camera is being controlled by a hand controller, and if the foot controller is attempted to be used to select an energy-output function (e.g., cauterize) by pushing on the cradle member toward an energy activation position, an actuator can be controlled by the system to prevent the cradle member from moving, and/or can push the cradle member away from the energy position.

Figure 5:
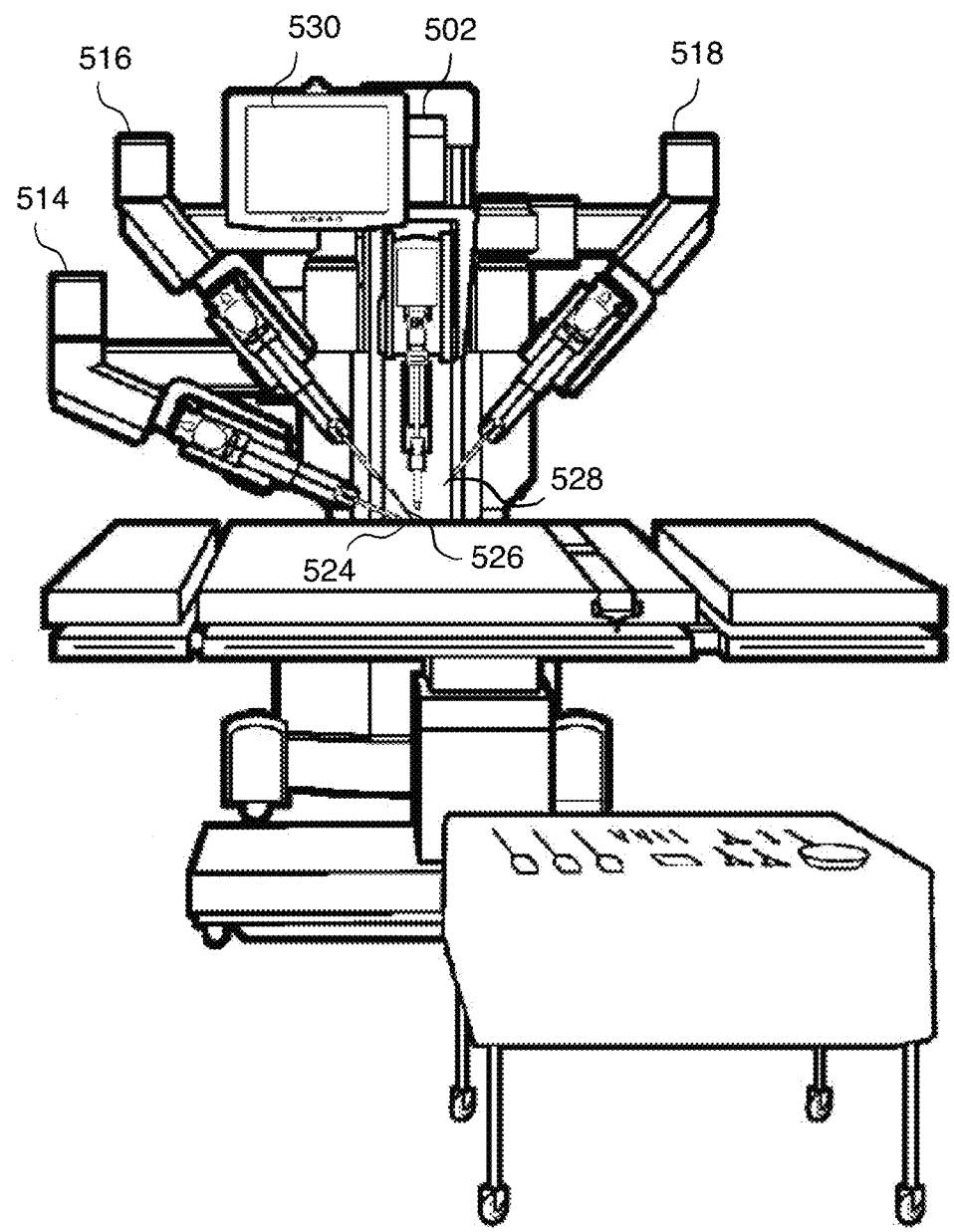
FIG. 5 is a diagrammatic illustration of an example teleoperated slave device and patient site.
Figure 6:
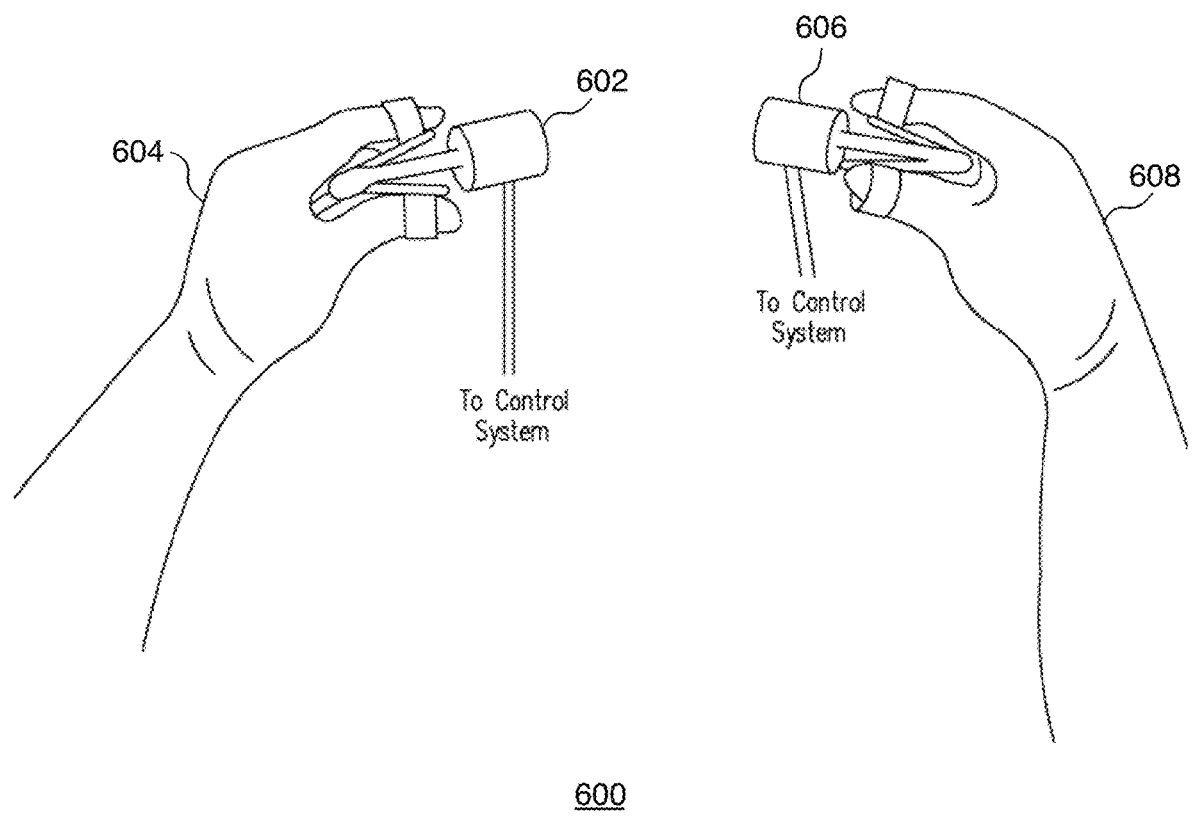
FIG. 6 is a diagrammatic illustration of example hand controllers, according to some implementations.

FIG. 5 is a diagrammatic illustration of an example teleoperated slave device and patient site 500 for an example teleoperated surgical system, which can be used with one or more features disclosed herein.

A manipulator slave device 502 can be controlled by one or more master controllers of a master control device. For example, one or more hand controllers 122 and foot controllers 120 as shown in FIG. 1 can be used to control slave device 502. During a surgical procedure, the slave device 502 can be positioned close to an operating table and patient (or simulated patient) for surgery, where it can remain stationary until a particular surgical procedure or stage of a procedure is completed. Slave device 502 can include one or more arm assemblies 514, 516, and 518. In some examples, one or more of the arm assemblies can be configured to hold an image capturing device, e.g., a camera of an endoscope, which can provide captured images of a portion of the surgical site. In some implementations, the captured images can be transmitted to the viewer of the workstation and/or transmitted to one or more other displays, e.g., a display coupled to the slave device. In some examples, each of the other arm assemblies may include a surgical tool 524, 526, and 528. Each surgical tool can include a surgical end effector, e.g., for treating tissue of the patient.

In this example, the arm assemblies may be caused to move and articulate the surgical tools in response to manipulation of the master controllers. This enables the user to direct surgical procedures at internal surgical sites through minimally invasive surgical apertures. For example, one or more actuators coupled to the arm assemblies can output force to cause links or other portions of the arm assemblies to move in particular degrees of freedom in response to control signals received from the master controllers. The master controllers can be used within a room (e.g., an operating room) that also houses the slave device and worksite (e.g., within or outside a sterile surgical field close to an operating table), or can be positioned more remotely from the slave device, e.g., at a different room, building, or other location than the slave device.

Some implementations of the teleoperated system can provide different modes of operation. In some examples, in a non-controlling mode (e.g., safe mode) of the teleoperated system, the controlled motion of manipulator slave device 502 is disconnected from the master controllers of the workstation in a disconnected configuration, such that movement and other manipulation of the master controls does not cause motion of the manipulator slave device. In a controlling mode of the teleoperated system (e.g., following mode), the motion of the manipulator slave device can be controlled by the master controls such that movement and other manipulation of the master controllers causes motion of the manipulator slave device, e.g., during a surgical procedure.

In other implementations that can make use of one or more foot controllers 120, the teleoperated surgical system can include a master control workstation (e.g., surgeon's console) (not shown) at which a user can sit or stand. In some examples, a support can be provided on which a user, e.g., an operator such as a surgeon, can rest his or her forearms while gripping two grounded master controllers. For example, the master controllers can be positioned in a workspace disposed inwardly beyond the support. When using the workstation, the user can sit in a chair in front of the workstation, position his or her eyes in front of the viewer and grip the master controllers, one in each hand, while resting his or her forearms on the support. In some implementations, the master control workstation may include a viewer where an image of a surgical site (or other work site) is displayed during an operating procedure using the slave device. For example, the image may also be displayed by a display device 530, such as one or more display screens, and may depict a surgical site during a surgical procedure. A operator at the workstation can operate one or more foot controllers 120 to control particular functions of the slave device and teleoperated system as described herein. For example, some implementations of a teleoperated medical system having a master control workstation can include a da Vinci® Surgical System (e.g., a Model IS3000 or IS4000, marketed as the da Vinci® Si® or da Vinci® Xi® Surgical System), commercialized by Intuitive Surgical, Inc. of Sunnyvale, Calif.

Features disclosed herein may be implemented in various ways, including teleoperated and, if applicable, non-teleoperated (e.g., locally-controlled) implementations. Implementations on da Vinci® Surgical Systems are merely exemplary and are not to be considered as limiting the scope of the features disclosed herein. For example, different types of teleoperated systems having slave devices at worksites can make use of actuated controlled features described herein. Non-teleoperated systems can also use features described herein.

In some implementations, a controlled slave manipulator device can be a virtual representation of device, e.g., presented in a graphical simulation provided by a computing device coupled to the teleoperated system 500. For example, a user can manipulate hand master controllers and foot controller(s) to control a displayed representation of an end effector in virtual space of the simulation and control virtual functions of the representation (or other virtual instruments) similarly as if the end effector were a physical object coupled to a physical slave device.

FIG. 6 is a diagrammatic illustration of one example of hand controllers, according to some implementations. Hand controllers 602 and 606 may act as master controllers in a teleoperated system to control various functions of a teleoperated slave device, and may be master tool grips in some implementations. In some implementations, hand controllers 602 and 606 are held by a user's hands and are mechanically ungrounded, e.g., unconstrained in position and orientation in space and not mechanically supported by supports attached to the ground. For example, hand controllers 602 and 606 may be operated by surgeon 102 in a standing position as shown in FIG. 1 or in a sitting position. In some examples, a surgeon may stand near a surgical site and, while standing, operate one or more hand controllers 602 and 606 as well as one or more foot controllers as described herein.

In some examples, surgeon 102 can use or manipulate hand controller 602 as a master tool grip to control a proxy visual (e.g., a manipulable camera included on the slave device or other device), and can use or manipulate hand controller 606 as a master tool grip to control teleoperated surgical instrument 114, 116, and/or 118. Other configurations are also possible, e.g., using both controllers 602 and 606 to control surgical instruments and/or other functions of the teleoperated system. In some examples, two finger grips of hand controller 602 and hand controller 606 can be moved together or apart by the surgeon in pincher motions to, for example, correspondingly move forceps, pliers, or other surgical instrument end effectors of a teleoperated slave device. In some implementations, the positions of the controllers 602 and 606 in three-dimensional space can be sensed (e.g., using sensors provided in controllers 602 and 606 and/or separate external environment sensors) to control functions of the teleoperated slave device.

Other types of hand controllers can be used in other system implementations that include one or more foot controllers described herein. For example, one or more mechanically grounded hand controllers can be provided, e.g., as components of a workstation or console coupled to ground and at which the user sits to operate the hand controllers and one or more foot controllers. For example, a grounded hand controller can be coupled to a mechanical linkage that is coupled to the ground or an object that is connected to ground, providing a stable platform for the use of the hand controller.

Figure 7:
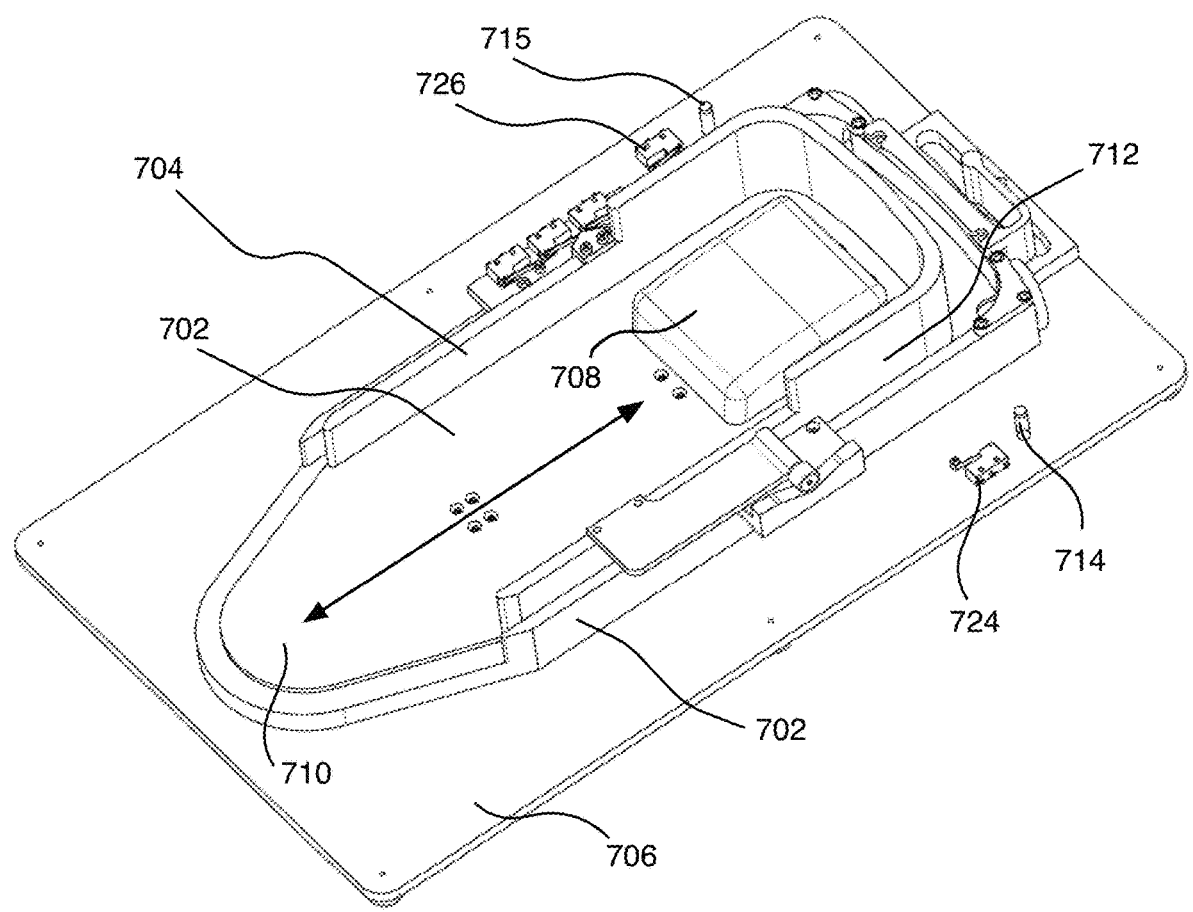
FIG. 7 is a top perspective view of another implementation of a foot controller, according to some implementations.

FIG. 7 is a top perspective view of another example implementation of a foot controller 700, according to some implementations. Foot controller 700 can be used by a single foot of a user. For example, foot controller 700 can be used by a standing user or by a sitting user, or may be used by a user alternately sitting and standing. Foot controller 700 can include a cradle member 704 provided on a base member 702, which in turn is provided on a stationary portion 706. In this example, cradle member 704 is moveable in a forward-back axis relative to base member 702, and base member 702 (together with cradle member 704) is moveable in a left-right axis relative to stationary portion 706. The cradle member can be moved by the user's foot to any of various activation positions and along paths similarly as described for implementations above.

In some implementations, the user's foot rests on cradle member 704, which moves or shifts along the forward-back axis relative to base member 702. In this example, base member 702 with cradle member 704 are configured to move together, approximately along the left-right axis, by pivoting within a limited path around a pivot axis perpendicular to the plane of pivot. In some examples, the plane of pivot can be parallel to the plane of forward-back motion of the cradle member. In some examples, the plane of pivot can be parallel to the surface of the stationary portion 706, which in turn can be parallel to the surface of the ground in some implementations. For example, the pivot axis can be located near the back side of the foot controller. For example, the pivot axis can be at or near a location 710, which can be near a location of the user's heel during user operation of the foot controller. In other implementations, the cradle member 704 and base member 702 can be moved linearly left and right relative to the stationary portion 706, e.g., rather than being pivoted as described.

A retaining protrusion or wall 712 of cradle member 704 can be provided, e.g., on the left and right sides of the cradle member and/or at the front of the cradle member. The terms protrusion and wall may be used interchangeably. The retaining wall can function to provide a surface against which the user can move his or her foot when moving cradle member 704 left or right. For example, a walls can serve to contain the foot within the cradle member, and/or to help guide the foot into the cradle member, and/or to make it easier for the user's foot to find the cradle member by feel without accidentally activating an input control. The wall can assist in maintaining the user's foot in the proper location in the cradle member. For example, shifting the cradle member forward and back can be powered with the heel of the user's foot, and pivoting the cradle member left and right can be powered with the sides of the front portion of the foot. In some implementations, the retaining walls 712 on the left and right can be of such height so as to allow the user's side foot portion to press against the walls 712 and pivot the cradle member without causing the user's foot to unintentionally press an activation control switch 708 positioned in the cradle member.

Base member 702 and cradle member 704 are shown in a center position. Base member 702 and cradle member 704 can pivot to the right and impact vertical stop pin 714 (a stop member) connected to the stationary portion, where the stop pin provides a stop to the right movement. At or near the stopped right position, base member 702 actuates a right limit switch 724 (e.g., positioned near the pin 714 in FIG. 7) which can be a sensor to detect the position of the cradle member and base member at a right position. Similarly, the base member 702 and cradle member 704 can pivot to the left and impact a stop pin 715 that stops the left movement. At or near the stopped left position, the base member 702 can activate limit switch 726 on the left side (e.g., near the left stop pin 715) that is connected to the stationary portion, where the limit switch can be a sensor to detect the position of the cradle member and base member at a left position. Other types of sensors can also or alternatively be used to sense the left, right, and other positions of the base member and cradle member along the left-right axis.

In some embodiments, one or more actuators can be used to output force on the base member and/or cradle member in the left-right degree of freedom of the base member and cradle member. In some embodiments, a damper can provide resistance to motion of the base and cradle members. In some examples, a viscous damper (e.g., linear plunger-style damper or rotary damper coupled via a transmission such as a rack and pinion) may be coupled between the base member 702 and a member coupled to the stationary portion 706, e.g., a stop pin 714 or 715 or switch 724 or 726. The damper can be coupled to a linkage connected between the base member 702 and the stationary portion 706 to provide force resistance in the left-right range of motion of the cradle member and base member. In some embodiments, the cradle member 704 can have freeform movement in a portion of the movement range before hitting the damper (e.g., freeform movement in a range centered at the center position of the base member), then receives damping after hitting a damper and moving toward the pins 714 or 715 when moving to the right position or left position. For example, a respective damper can be positioned near pins 714 and 715 and engaged by the base member when pivoting close to the associated pin. This allows the cradle member and base member to move out of the left or right position, towards the center position, without receiving resistance from the damper. In some implementations, the limit switches are sensors which sense the base member and cradle member reaching an end of travel in the left or right direction. In some implementations, one or more sensors can be used to sense additional and/or continuous positions of the cradle member and/or base member, e.g., between the center position and the end of travel in a left or right direction. In some implementations, one or more dampers may be used to provide viscous friction or to provide coulomb friction (e.g., using coulomb damping). An advantage of using coulomb friction is that the amount of friction is proportional to the amount of force applied by the user's foot onto the cradle member (e.g., force applied perpendicular to the plane of left-right motion). This type of friction may cause more difficult sliding of the cradle member for a heavy application of the foot due to greater applied friction, and likewise enables easier sliding of the cradle member for a lightly-applied foot. Additional implementations are described in more detail herein.

In this implementation, stationary portion 706 is flat. In some implementations, stationary portion 706 can be of varying elevation similarly as described above for FIG. 2.

Activation control foot switch (or button) 708 can be an input control similarly as described above, and is positioned on cradle member 704. For example, the foot switch 708 can be activated (e.g., pressed) by a front portion of the user's foot. In some implementations, the foot switch may have an integral limit switch. Other types of input controls can be used in other implementations.

In some implementations, downward force of a foot on cradle member 704 may be detected (e.g., with or without activation of the foot switch 708). For example, in some implementations, proximity sensors can be used. In further examples, a strain gauge may be embedded at an appropriate location, e.g., on cradle member 704. Various ways to measure force, e.g., by sensing movement, may include displacement sensors, or optical sensors to detect downward movement of cradle member 704 caused by a foot pressing down on the cradle member 704.

In some implementations, a location where the foot is positioned on cradle member 704 (e.g., a location of a toe and/or heel of the user's foot) can be sensed, e.g., using optical, ultrasonic, or capacitive sensors. Sensing the force (e.g., downward force) of the user's foot on the cradle member can also or alternatively be sensed. In some implementations, sensing the downward force can be a secondary confirmation of sensing the location of the foot on cradle member 704. In some implementations, system functions are enabled to be activated using the foot controller in response to sensing the user's foot, or portions thereof, in one or more predetermined locations of the cradle member 704 and/or foot controller. For example, a user can be required to have the heel of the foot down or contacting the cradle member 704 (or other component of foot controller 700) before the foot controller can activate functions.

Figure 8:
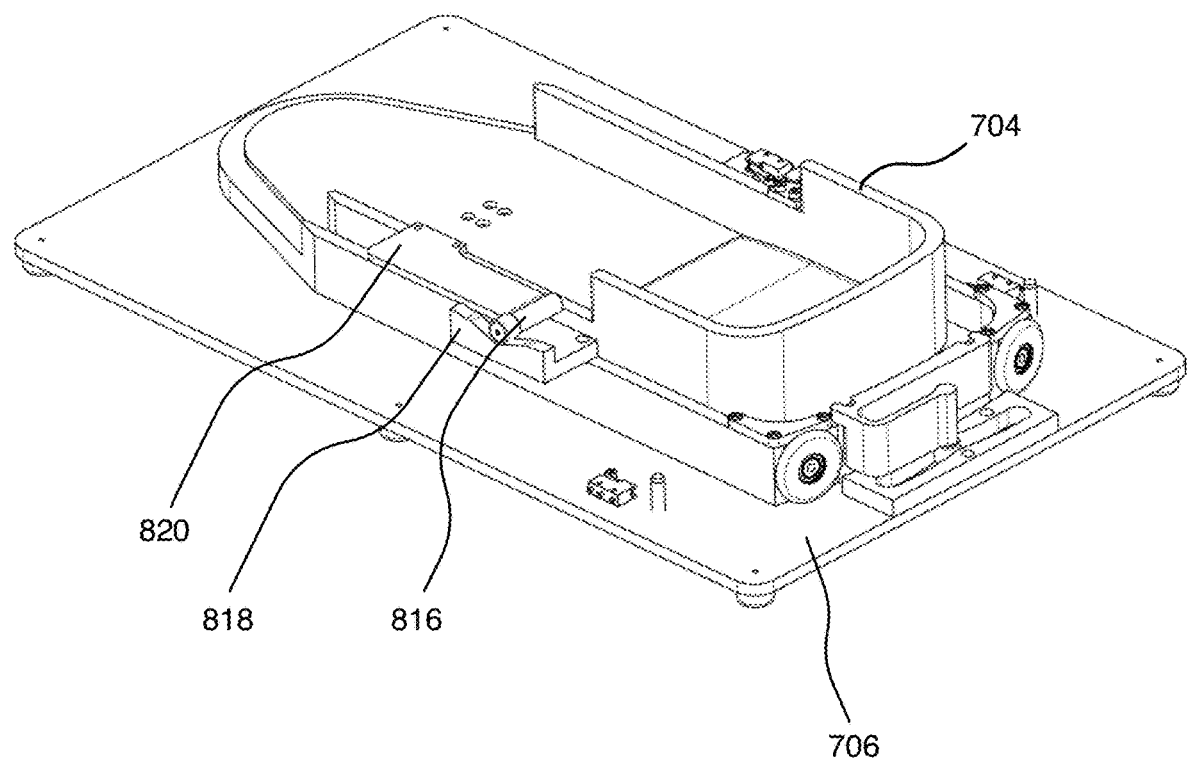
FIG. 8 is a side perspective view of the foot controller of FIG. 7, according to some implementations.

FIG. 8 is a side perspective view of the foot controller of FIG. 7, according to some implementations. In some implementations, a restoring force (e.g., a constant restoring force) can be provided on cradle member 704 that physically biases the cradle member to move toward (or stay in) a neutral (e.g., center or origin) position in its degrees of freedom (e.g., left-right and forward-back axes). This may include a restoring force when the user eases up a foot resting on cradle member 704. The restoring force can be provided by a variety of types of mechanisms coupled to the cradle member and/or base member. In the example of FIG. 8, a cam mechanism is used, including one or more cams and associated cam followers. In some implementations, as described below, the cam can include a surface having a varying slope to provide a varying amount of restorative force to the cradle member at different positions in the degree of freedom. In some implementations, the center position of the cradle member corresponds to a particular position (e.g., an elevation) of the cam to which the cam follower is biased to move from positions adjacent to the center position, e.g., the particular position is lower in elevation than positions adjacent to the center position.

Cam 818 and cam follower 816 provide restorative force to the cradle member 704 along the forward-back axis. Cam follower 816 includes a roller that rolls on the surface of cam 818. Cam 818 is rigidly coupled to the base member 702. In this example, cam 818 includes a surface having a slope, e.g., from a lowest point at the center of the cam surface to higher points on either side of the lowest point, forming a "V" shape. The cam follower is biased to move to the lowest point of the V shape.

In some implementations, cam follower 816 is attached to flexure 820, where the flexure biases the cam follower 816 against the surface of the cam 818, e.g., the flexure provides a downward force of cam follower 816 on cam 818. The flexure can be flexed to allow the cam follower 816 to follow the changing slope of the surface of cam 818. Flexure 820 is coupled to the cradle member 704 and slides forward and back along with the cradle member in the forward-back axis relative to the base member 702, thus causing the cam follower 816 to roll along the surface of cam 818.

Flexure 820 is a spring element (e.g., plastic or metal) that can provide, at least in part, a restoring force to cradle member 704, e.g., in its forward-back movement, based on the position of the cam follower on the cam. The slope on cam 818 biases cam follower 816 into a lower energy location, e.g., the middle of the V shape of cam 818. For example, the cam follower 818 can be configured to be positioned at the lowest point of the surface of cam 816 when the cradle member 704 is positioned at a center or neutral position along the forward-back axis. In some implementations, if cradle member 704 is at the neutral position, cam follower 816 is at the center of the V shape, and more force is required from the user to move the cradle member out of its neutral position than into the neutral position. Flexure 820, cam 816, and cam follower 818 can be configured to bring the cradle member 704 back to the neutral position, e.g., when the user's foot has been removed after the user has moved the cradle member away from the neutral position in the forward-back axis.

In some implementations, as shown, cam 818 may have a surface that varies in slope, e.g., has two or more slopes. For example, a steeper slope can be provided in the middle of the V shape, and the slope of the cam 818 can be reduced (shallower) near the ends of the cam (at the ends of the V shape), where the cam surface flattens in an end zone at each end of the cam. In FIG. 8, the varying slope is implemented as multiple successive flat cam surfaces. Alternatively, a continuously curved cam surface can be used (as in cam 910, below). A smaller magnitude of restoring force is provided to the cradle member when the cam follower is at one of these end zones. The end zones of the cam can correspond to the portions of the path of the cradle member 704 that are near the end of its travel. This configuration allows the cradle member to be moved more easily at positions further away from the neutral position, e.g., when the cradle member is closer to an activating position. The configuration also may make it easier for the user to hold a particular position of the cradle member after the cradle member has been moved to that position (e.g., to use the input control 708s), but harder to intentionally move the cradle member to that position from a different position. For example, if cradle member 704 is near an activation position (that is not the center position), less force is needed to push cradle member 704 into that activation position (in the forward-back axis). When the cradle member is moved back to the center position, the greater slope of the central V-shape provides more force that biases cradle member 704 toward the center, e.g., due to force from the flexure 820 and/or gravity. In some implementations, the cam mechanism can be positioned on a different side of foot controller 700, and/or additional cams and cam followers can be included in foot controller 700, e.g., on one or more different sides of the foot controller.

In some implementations, additional changes in elevation can be provided in the cam 818. For example, additional dips or "valleys" can be placed in the cam 818 to correspond to positions of the cradle member at which a restoring force or bias is desired. For example, an additional lowered elevation can be positioned at the ends of the cam 818 that correspond to activation positions of the cradle member at its ends of travel in the front-back axis. In some examples, an activation position of the cradle member can have a corresponding elevation of the cam that is lower than cam elevations corresponding to positions of the cradle member adjacent to the activation position. Such features can provide force biasing of the cradle member from one of the positions adjacent to the activation position toward the activation position.

Figure 9:
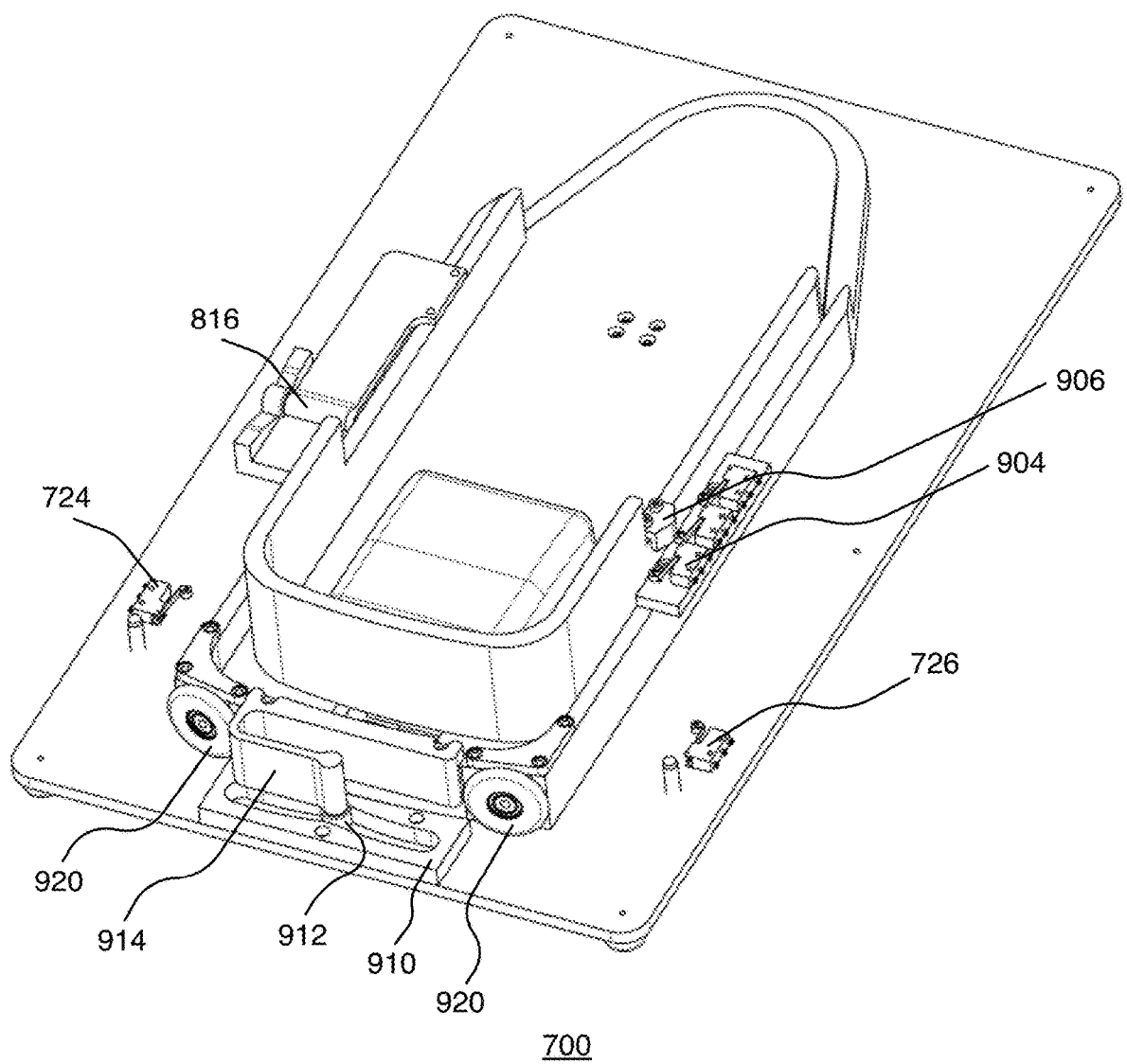
FIG. 9 is an end perspective view of the foot controller of FIG. 7, according to some implementations.

FIG. 9 is an end perspective view of the foot controller of FIG. 7, according to some implementations. Limit switches 724 and 726 detect an activation position of the pivoting cradle member 704 and base member 702 at the left or right ends of travel in the left-right axis, as described above with reference to FIG. 7.

Switches 904 can be used as sensors that detect the forward-back sliding position of cradle member 704, e.g., relative to base member 706. For example, in the example shown, switches 904 can include multiple (e.g., three) switches arranged linearly in the forward-back axis, each switch coupled to the base member 702. A trigger element 906 can be coupled to the cradle member 704 and is configured to activate each switch 904 when moved past the switch 904. As the cradle member 704 is moved forward or back, the trigger element 906 passes each switch 904 in turn, activating the switch as it passes. Multiple positions of the cradle member 704 can thus be sensed in the forward-back axis. In some implementations, a switch 904 can be placed at each end of travel of the cradle member 704 in the forward-back axis to sense forward and back activation positions of the cradle member. Alternatively or additionally, other types of sensors can be used to sense positions of the cradle member 704 in the front-back axis, e.g., optical sensor, magnetic sensor, etc.

In some implementations, a restoring force can be provided on cradle member 704 that physically biases the cradle member to move to a neutral (e.g., center or origin) position in its left-right axis or degree of freedom, e.g., similar to the restoring force described above for the forward-back axis or degree of freedom in FIG. 8. The restoring force can be applied in the pivoting degree of freedom of the cradle member 704 and base member 702. The restorative force can be provided by a variety of types of mechanisms coupled to the cradle member and/or base member. In the example of FIG. 9, a cam mechanism is used, including one or more cams and associated cam followers. Similar to the cam mechanism described for FIG. 8, the cam can include a surface having a varying slope to provide a varying amount of restorative force to the cradle member at different positions in the degree of freedom. In some implementations, the center position is at a lower-energy position of the cam to which the cam follower is biased to move from positions adjacent to the center position.

In this example, a cam mechanism includes cam 910 and cam follower 912. Cam follower 912 includes a roller that rolls over the surface of cam 910. Cam 910 is rigidly coupled to the stationary portion 706, e.g., at the front side of the foot controller 700 in this example. In the example of FIG. 9, cam 910 includes a surface that has a lowest-energy position at or near the center of the cam surface and higher-energy positions on either side of the lowest-energy position, forming an approximate "V" shape. In this example, the slope of the cam surface varies, where the varying slope allows a force-distance profile to be explicitly configured to a custom configuration. In some implementations, the varying slope can be a linearly varying relationship (Hooke's law). For example, a steeper (higher) slope is provided closer to the lowest-energy position and a more shallow (lower) slop is provided further from the lowest-energy position. In this example, a continuously-varying slope is used to provide a curved cam surface, in contrast to the multiple successive flat cam surfaces of cam 818. Alternatively, a cam surface as used for cam 818 can be used in cam 910.

Cam follower 912 is attached to flexure 914, where the flexure biases the cam follower 912 against the surface of the cam 910. The flexure can be flexed to allow the cam follower 912 to follow the changing slope of the surface of cam 910. Flexure 914 is coupled to the base member 702 (e.g., at a front of the base member 702) and pivots with the base member in the left-right axis relative to the stationary portion 706, thus causing the cam follower 912 to roll along the surface of cam 910. For example, flexure 914 can be a spring element (e.g., plastic or metal) that contributes to a restoring force to cradle member 704 and base member 702, e.g., in its left-right movement, based on the position of the cam follower on the cam. The slope on cam 910 biases cam follower 912 into a lower energy position, e.g., the middle of the V shape of cam 910. For example, the cam follower 912 can be configured to be positioned at the lowest point of the surface of cam 910 when the cradle member 704 is positioned at a center or neutral position along the left-right axis. In some implementations, if cradle member 704 is at the neutral position, cam follower 912 is at the center of the V shape, and more force is required from the user to move the cradle member out of its neutral position. Flexure 914, cam 910, and cam follower 912 can be configured to bring the cradle member 704 back to the neutral position, e.g., when the user's foot has been removed or eased up after the user has moved the cradle member away from the neutral position in the left-right axis.

The varying slope of the surface of cam 910 can provide varying magnitudes of restoring force that bias the cam follower and cradle member/base member to their center position. For example, a larger magnitude of restoring force is provided to the cradle member when the cam follower is at or closer to the lowest-energy position of the cam surface, which resists movement away from the center position and/or biases movement toward the center position. A smaller magnitude of restoring force is provided to the cradle member when the cam follower is further from the lowest-energy position of the cam surface, e.g., corresponding to the portions of the path of the cradle member 704 that are near the end of its travel in the left-right degree of freedom. This configuration allows the cradle member to be moved more easily at positions further away from the center position, similarly as described above for FIG. 8. In some implementations, the cam mechanism can be positioned on a different side of foot controller 700, and/or additional cams and cam followers can be included in foot controller 700, e.g., on one or more different sides of the foot controller.

In some implementations, additional changes in elevation can be provided in the cam 910. For example, additional dips or "valleys" can be placed in the cam 910 to correspond to positions of the cradle member at which a restoring force or bias is desired, such as at the ends of the cam 910 that correspond to activation positions of the cradle member at its ends of travel in the left-right axis.

One or more rollers 920 can be coupled to one or more components of the foot controller to assist in pivoting base member 702 and cradle member 704. In some implementations, as shown, rollers 920 are coupled to base member 702 and positioned at the front of the base member. In some examples, the rotational axes of rollers 920 extend through the center of rotation of the heel rotational bearing. Rollers 920 allow the base member to pivot smoothly without scraping the stationary portion 706. For example, a heel pivot bearing (see FIG. 10) can provide constrained movement of the base member in a horizontal plane, but may not prevent the front part of the base member 702 and cradle member 704 from bending down toward the stationary portion 706, which may cause the base member to scrape the surface of the stationary portion 706. Rollers 920 can be wheels used to support the front of the cradle member 704, e.g., hold up the front end of base member 702 and allow the base member to pivot with respect to the stationary portion 706 without scraping between base member 702 and stationary portion 706.

In some implementations, one or more rotary actuators may be coupled to one or more of rollers 920 to provide haptic feedback to the cradle member in the left-right degree of freedom. In some examples, a roller 920 can be gear-toothed, and driven with a motor. The roller may move within a toothed or curved track (or groove) to provide traction between the roller and the surface of stationary portion 706.

In some implementations of either or both cam mechanisms of FIGS. 8 and 9, the provided restoring force is continuously present on the cradle member 704, and a lock may be provided to hold cradle member 704 in the center position. The lock can be positioned in various locations on the foot controller. The lock can be, for example, implemented using a linear or rotary electromagnetic brake or other type of brake to output resistive force preventing normal operating movement of the cradle member. Alternatively, an electromagnet can energize a coil to provide locking force. For example, a magnetic field may be applied to lock a friction pad in place, and when the field is removed, the cradle member 704 can travel. In another example, a physical lock can include a solenoid actuator holding onto (e.g., braking) a cam follower and preventing or reducing the cam follower from rolling or moving unless the solenoid is activated. In another example, a physical lock can include a solenoid actuator inserting a locking member (e.g., a tooth) into an opposing part and preventing the pair of parts from moving. Alternatively, a friction brake can be provided on one or more of the rollers 920 (e.g., at the front of the base member 702) to provide locking or resistive friction forces. In some implementations, a friction brake can be provided between cradle member 704 and base member 702, or between base member 702 and stationary portion 706 to provide locking or resistive friction forces. In some implementations, a brake can be back-driven, or a safety lock can be used.

Figure 10:
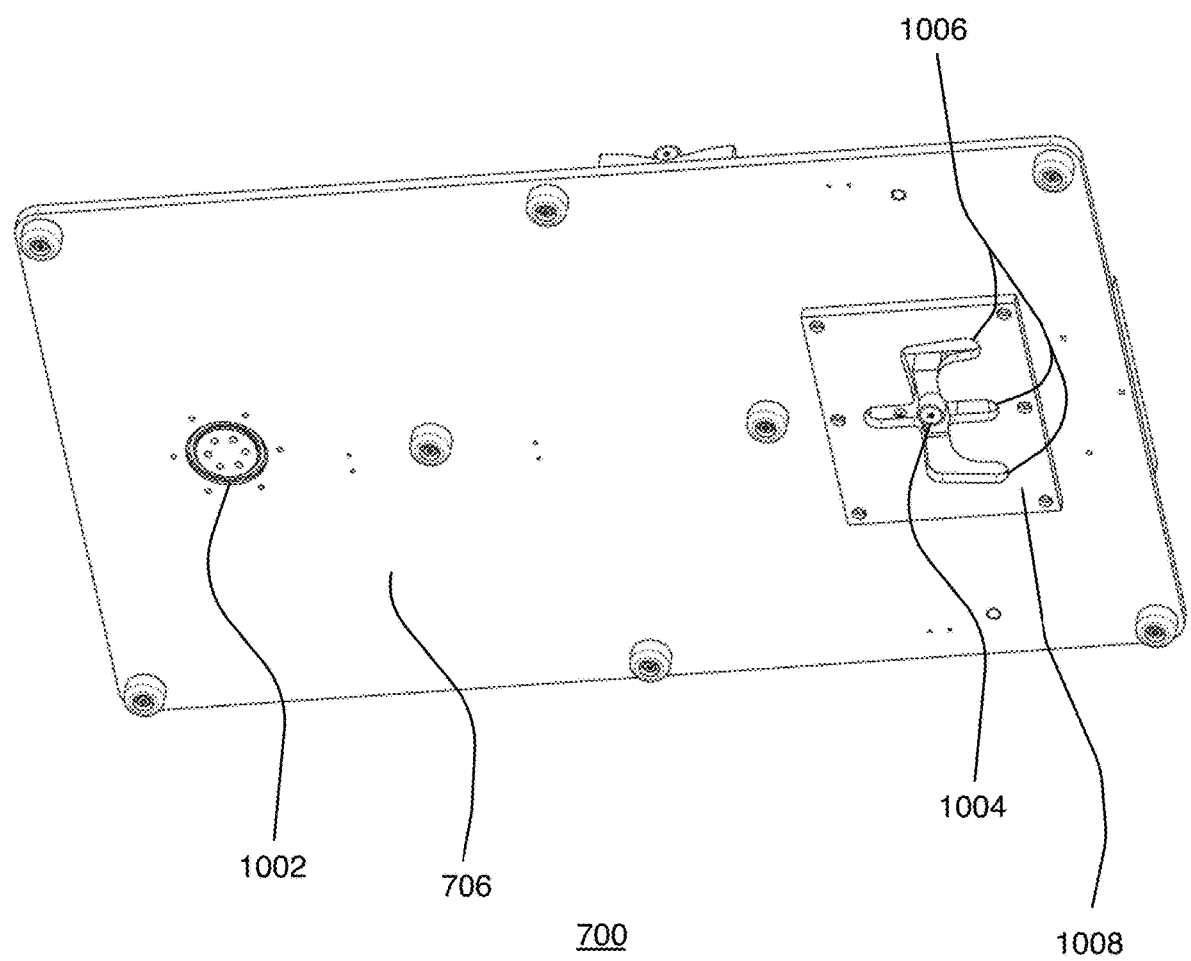
FIG. 10 is a bottom perspective view of a stationary portion of the foot controller of FIG. 7, according to some implementations.

FIG. 10 is a bottom perspective view of the stationary portion 706 of the foot controller 700 of FIG. 7, according to some implementations. A view of an example underside of the stationary portion 706 is shown. Heel pivot bearing 1002 connects base member 702 to stationary portion 706 and allows the base member 702 to rotate with respect to the stationary portion 706.

Cradle element 1004 is coupled to cradle member 704 and extends through the base member 702 into a guide 1006 provided in the stationary portion 706. Guide 1006 includes one or more grooves or holes that constrain the movement of the cradle element 1004 and cradle member 704 to one or more paths that guide the cradle member to the activation positions that provide commands to activate functions of the connected system. In this example, guide 1006 is trident-shaped, having a center groove (in a forward-back alignment) and two symmetrical elbow grooves that extend left and right perpendicularly from the center of the center groove and extend toward the front of the foot controller approximately parallel to the center groove. Guide 1006 provides paths for cradle element 1004, where the trident-shaped grooves of guide 1006 constrain motion of the pedal to the paths within the trident shape. The grooves provide opposing forces to the cradle member 704 when the cradle element 1004 is moved into a wall of a groove in the guide 1006. These forces can reassure the user that a desired pathway is being taken and/or a desired position of the cradle member has been reached.

In some implementations, a cradle member position (e.g., activation position or end position) may be designated at each elbow joint of guide 1006, which can be the positions at the end of travel straight left or straight right from the center position of the guide, without moving forward).

Other configurations of grooves can be provided in the guide 1006 in some implementations. For example, a cross-shaped guide, H-shaped guide, I-shaped guide, T-shaped guide, or other shaped guide can be used. In some implementations, the guide 1006 can be a diamond shape or any polygonal shape (hexagon, octagon, square, circle, oval, etc.), allowing free movement of the cradle element 1004 within the polygonal shape, and where, for example, paths intermediate to activation positions are not defined. For example, activation positions can be defined at particular positions along the edges and/or corners of the walls of a polygonal shape.

In some implementations, there may be curves provided in one or more of the paths of the guide, e.g., a curved path provided to each activation position of the cradle member 702. In some implementations, different paths of the guide can be provided with respectively distinct or noticeable feels to the user of the foot controller, e.g., based on the angle or degree of curvature of the paths.

In some implementations, one or more paths of the guide can be provided with distinct or noticeable feels to them based on tactile elements provided in the paths. For example, tactile elements can be provided on the walls of the grooves forming guide 1006 (e.g., bumps, undulations, or other features). In some implementations, different paths can be provided with respectively different feels to the user of the foot controller.

In some implementations, the guide 1006 may be provided on a plate 1008 that may be removed from the stationary portion 706 and replaced with a different plate that has a differently-shaped guide, or to provide an open space where plate 1008 is positioned. In some implementations, plate 1008 can be removed to provide a different plate having a guide and/or one or more actuators or sensors to detect movement of cradle element 1004.

In some implementations, e.g., where open space is provided in place of one or more grooves of guide 1006, one or more paths may be created by using actuator forces output by one or more actuators. For example, a controller may sense which direction the user is pushing the cradle member to get to an activation position. Guided paths can be enabled by controlling the one or more actuators to output forces to simulate walls of a guide at particular positions of the cradle member 702 and/or cradle element 1004 and in particular directions of movement. In this way, provided paths can be variable and programmable based on the output of forces from the one or more actuators. Some examples of actuators providing forces in degrees of freedom of the cradle member 702 are described with reference to FIGS. 13-16.

Figure 11:
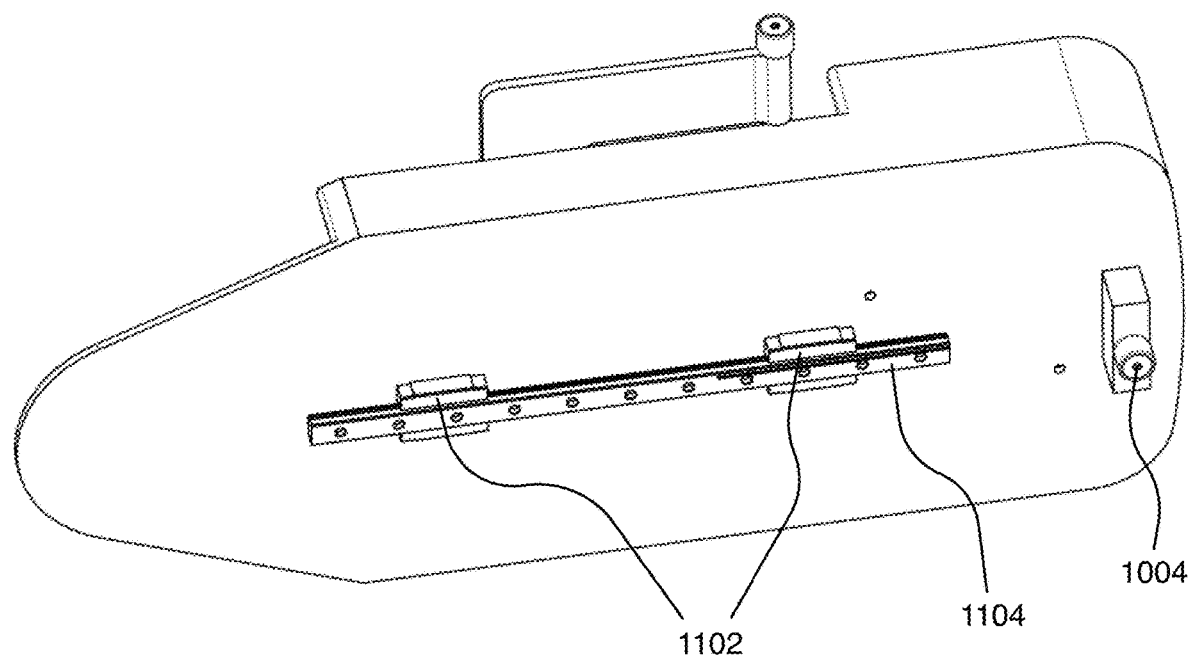
FIG. 11 is a bottom perspective view of a cradle member of the foot controller of FIG. 7, according to some implementations.

FIG. 11 is a bottom perspective view of a cradle member 704 of the foot controller 700 of FIG. 7, according to some implementations. In this example, a linear bearing is coupled between the cradle member 704 and base member 706 to provide linear motion between cradle member 704 and base member 702. For example, the linear bearing can include guide members 1102 and linear rail 1104, where linear motion is provided between guide members and rail. In some examples, the rail 1104 can linearly slide between the guide members 1102. In some implementations, rail 1104 is rigidly coupled to base member 702 and guide members 1102 are rigidly coupled to cradle member 704. In some implementations, rail 1104 is rigidly coupled to cradle member 704 and guide members 1102 are rigidly coupled to base member 702. In some implementations, the linear bearing can be an anti-friction bearing, e.g., ball bearings can be used in the guide members 1102.

In some implementations, haptic feedback can be added to the foot controller in the form of friction added to the forward-back linear bearing. For example, the slope or angle of the rail 1104 may be changed to produce more friction with the guide members 1102. In some examples, the slope or angle of the linear rail 1104 is changed in one or more portions of the rail 1104 (e.g., not the entire rail) to provide different amounts of friction at different positions, zones, or ranges of positions of the forward-back degree of freedom. For example, a portion of the rail 1104 centered on the center position of the cradle member can be angled to provide more friction, while other portions of the rail (e.g., near the ends of the rail) can provide less friction. In some implementations, similar friction can also or alternatively be added in the pivoting degree of freedom of the cradle member and/or base member, e.g., to the pivot bearing 1002 shown in FIG. 10 and/or rollers 920 shown in FIG. 9. The friction can be provided in the entire pivot degree of freedom and/or in one or more particular positions or sub-zones in the pivot degree of freedom.

Some implementations can make use of friction provided in one or more of the degrees of freedom of the cradle member and/or base member movement, where the friction is caused by the downward force or pressure of the user's foot on the cradle member and/or base member. For example, a sleeve bearing can be used for the linear bearing (e.g., including a bearing surface of metal or plastic) that includes elements that contact under foot pressure, such that friction increases in horizontal plane movement of the cradle member (left-right and/or forward-back) as the user's foot puts more force on cradle member 704.

In some implementations, when the user's foot presses on the activation input control 708 (e.g., button), the downward force may not be not purely downward and there may be a horizontal force component to the force that may cause the cradle member or base member to unintentionally move. In some implementations, adding friction to the movement of the cradle member (e.g., coulomb friction based on downward foot pressure as described above) can lock or bias the cradle member into its current position for input control activation, and thus may assist the user to push or otherwise activate the input control 708 without having to provide force exactly straight down (e.g., perpendicular to the bottom surface of the cradle member 704). In some implementations, cradle member 704 can be locked into place with brakes, latches, or other actuators.

In some implementations, friction and/or haptic feedback can be provided to cradle member 704 using a mechanism coupled between cradle member 704 and base member 702. For example, rollers moving into detents in grooves can provide haptic feedback. In some examples, guide members 1102 and rail 1104 may be replaced or supplemented by rollers provided on the bottom or sides of cradle member 704, which can roll within grooves or tracks in the surface of base portion 702 for forward/back movement. For example, four wheels, e.g., one wheel at each corner of cradle member 704, may move within tracks in the base member which constrain movement of the cradle member to directions forward and back. In some implementations, detents (e.g., divots) and/or other tactile elements may be placed in those tracks. For example, the tracks can include vertical undulations to vary the feel of movement of the cradle member in the forward and back directions.

Some implementations may incorporate a tilted or wedge-shaped stationary portion 706 or 206 (e.g., a ramp, one example of which is shown in FIGS. 2A-2E), yielding inclined operation of the cradle member. In a foot controller providing rolling or sliding cradle member, this tilt can assist to maintain the foot pedal in a defined location. This tilted surface can be used instead of or in addition to providing a restoration force or other force (e.g., using springs) that bias the cradle member into lower-energy locations (e.g., a center position), where the cradle member is biased to stay. In some implementations using a tilted or inclined stationary portion, the weight of the user's foot can be used to maintain the cradle member in detents or dips provided in a groove or track used to implement cradle member travel as described herein. Lifting weight off of the cradle member may allow easier motion of the cradle member. In some implementations, the user may perceive the cradle member travel due to haptic sensations providing haptic feedback, e.g., one bump can indicate the cradle member is being moved to a camera control position, a different magnitude or frequency of bump can indicate movement to a position controlling a clutch (e.g., a control to initiate a non-controlling mode for a teleoperated device).

Figure 12:
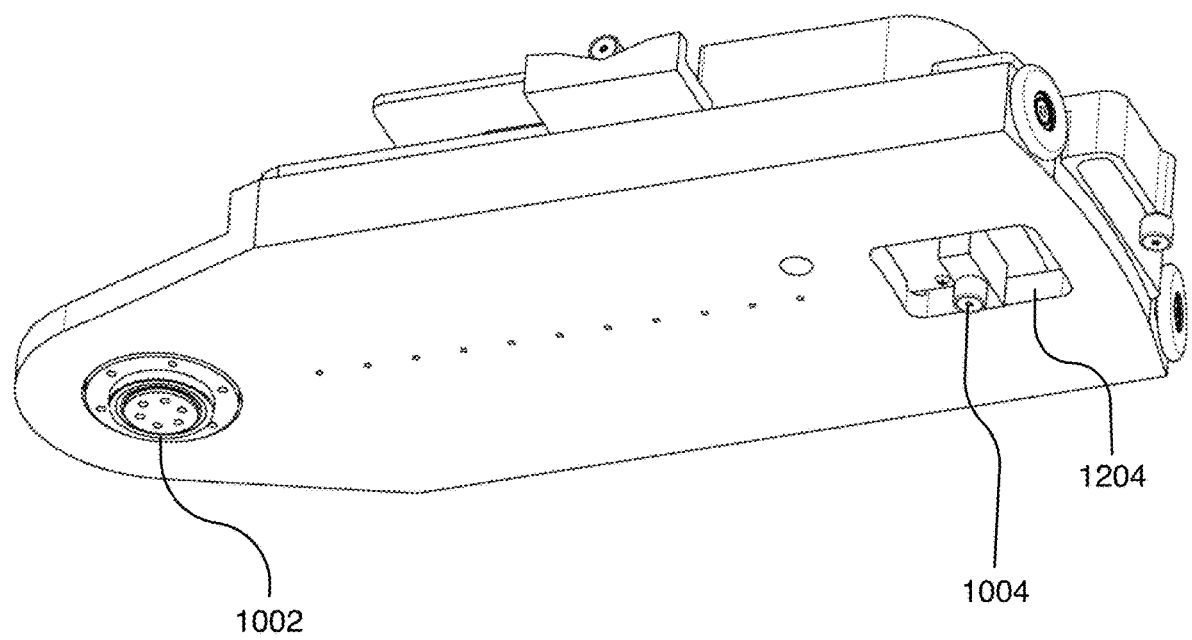
FIG. 12 is a bottom perspective view of a base member of the foot controller of FIG. 7, according to some implementations.

FIG. 12 is a bottom perspective view of an assembly 1200 of base member 702 and cradle member 704 of the foot controller 700 of FIG. 7, according to some implementations. FIG. 12 shows an example underside of base member 702. As shown, base member 702 receives a cradle member 704, e.g., on the top of the base member. Base member 702 is coupled to heel pivot bearing 1002 that rotatably connects the base member to the stationary portion 706, allowing the base member (and cradle member) to pivot with respect to the stationary portion 706.

An aperture 1204 can be provided through base member 702 to allow cradle element 1004 to be extended through the aperture 1204 and engage the guide 1006 of the stationary portion 706 shown in FIG. 10. Aperture 1204 also allows the cradle element 1004 to be moved forward and back within the aperture 1204 as cradle member 704 is moved forward and back relative to base member 702.

FIGS. 13-16 illustrate various views of an example implementation of a single-foot controller that includes linear motors that assist the user in manipulating the single-foot controller. For convenience, elements in the example implementations of FIGS. 13-16 that are similar to elements of the implementations of FIGS. 7-12 are referred to with similar names and/or reference numbers as in FIGS. 7-12.

Figure 13:
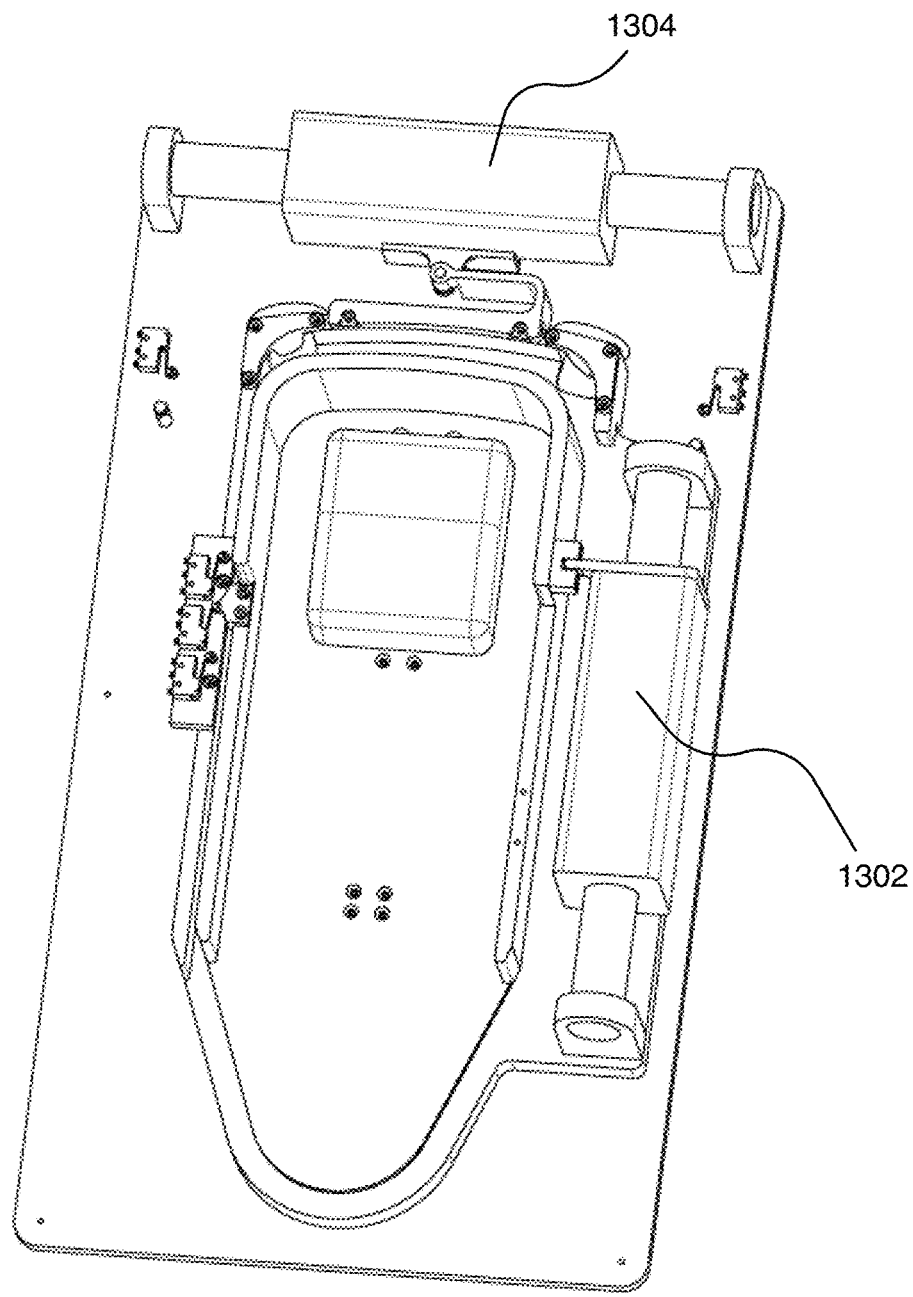
FIG. 13 is a top perspective view of another implementation of a foot controller, according to some implementations.

FIG. 13 is a top perspective view of an example foot controller 1300 according to some implementations. Controller 1300 includes two linear motors 1302 and 1304 to output forces in the two degrees of freedom of the cradle member 704 (e.g., as in FIG. 7) based on control signals provided from a controller (e.g., processor or device). Each linear motor 1302 and 1304 includes a forcer that is forced linearly along a stator based on the control signals. Other types of actuators may alternatively be used to provide linear forces, e.g., an electric motor-driven ball screw, an electric motor with rack and pinion drive train, or an electric motor using a capstan, belt, or cable drive, or a fluid-powered cylinder such as an air-cylinder or hydraulic cylinder. In some implementations, the cradle member position is back-drivable for safety reasons, which may preclude the use of lead screws, worm gears, etc. in an actuator transmission.

In some implementations, the degrees of freedom of the cradle member that receive actuator forces may include position sensing to allow actuator commutation and closing a loop on position control. For example, switches or other types of sensors can be used on the foot controller components as described herein and/or as components included in the actuators.

Figure 14:
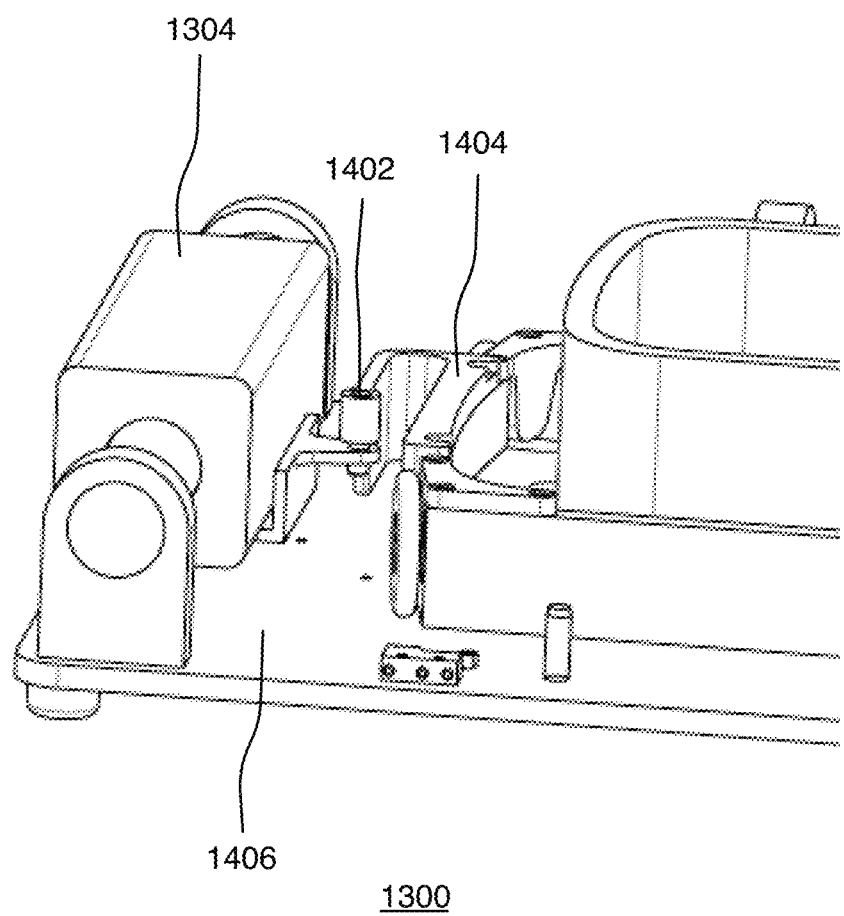
FIG. 14 is a perspective view of a front portion of the foot controller of FIG. 13, according to some implementations.

FIG. 14 is a perspective view of a front portion of foot controller 1300, according to some implementations. A flexure 1404 is coupled to the base member 702 (and thus cradle member 708) at one end of the flexure and has a spring effect allowing flex. The other end of the flexure 1404 is coupled to a tab that is coupled with a pin in a hole to allow pivoting, to a linear motor forcer of the linear actuator 1304 that is coupled to the stationary portion 1406. For example, the flexure 1404 can be rotatably coupled to the tab by a pin 1402 that extends through the flexure and tab. The flexure 1404 transmits force from the linear motor to the pivoting base member and pin 1402 rotates in the hole in which it is placed. This mechanism provides a slip fit hole arrangement that may avoid over-constraint of the flexure in the pivoting degree of freedom of the base member 702.

Figure 15:
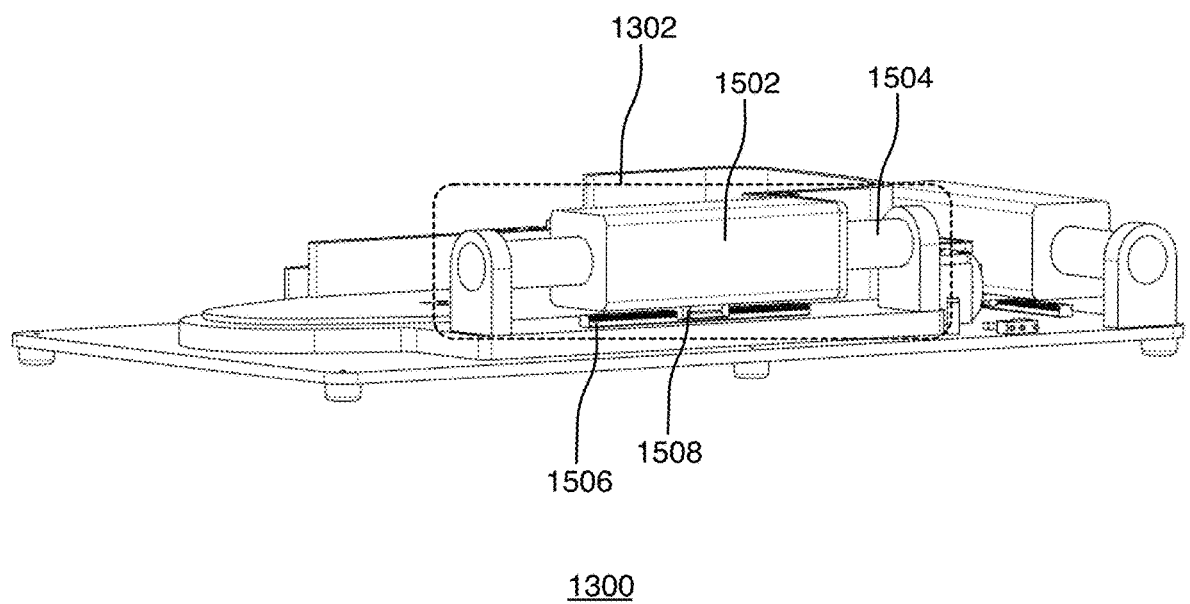
FIG. 15 is a side perspective view of the foot controller of FIG. 13, according to some implementations.

FIG. 15 is a side perspective view of foot controller 1300, according to some implementations. Linear motor 1302 is shown, which includes a linear motor forcer 1502 and a linear motor stator 1504. In this example, linear motor forcer 1502 is coupled to a linear slide block 1508, e.g., which is positioned on the underside of the forcer. Linear slide block 1508 engages with linear slide rail 1506 that is coupled to the base member 702 of the foot controller 1300. The linear slide block 1508 moves linearly along linear slide rail 1506 to constrain and guide the movement of linear motor forcer 1502 along its linear axis. For example, the linear slide block 1508 can include recirculating balls. Other types of linear couplings can be used in other implementations. The other motor, linear motor 1304, can include a similar linear slide block and linear slide rail, where the linear slide rail is coupled to the stationary portion 706 of the foot controller 1300.

Figure 16:
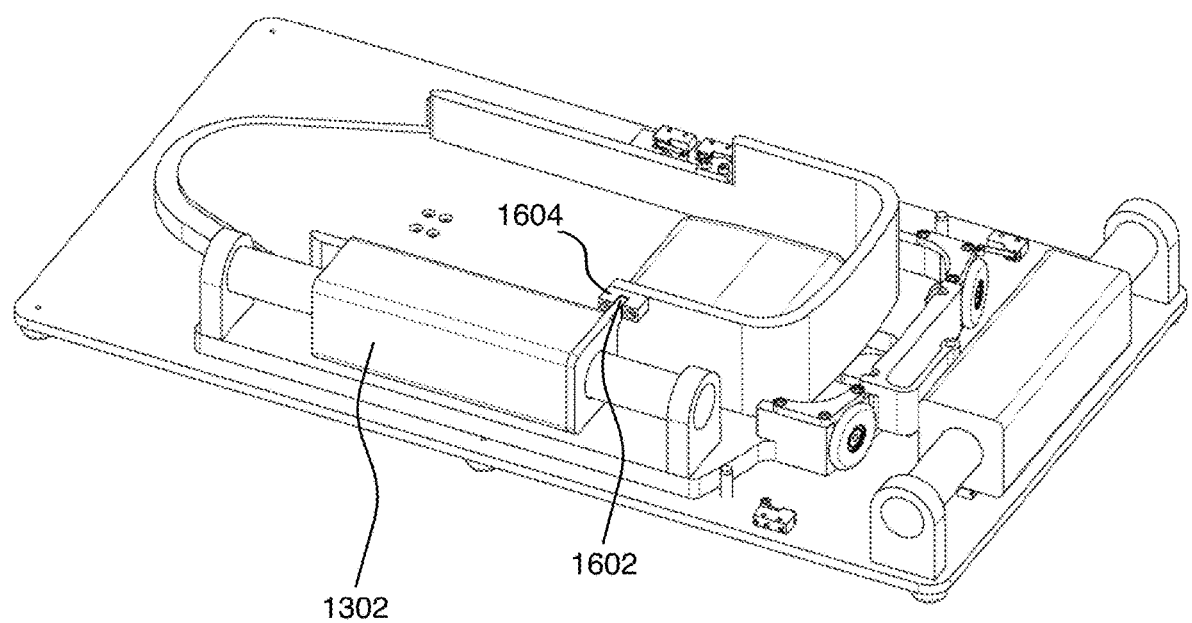
FIG. 16 is a top perspective view of the foot controller of FIG. 13, according to some implementations.

FIG. 16 is a top perspective view of single-foot controller 1300, according to some implementations. Linear motor 1302 has a stator coupled to the base member 702 and a forcer moving on the stator. Linear motor 1302 is also coupled to the cradle member 704. In some implementations, linear motor 1302 includes a tab 1602 coupled to the linear motor forcer of motor 1302, where the tab extends into a slot of a block 1604 coupled to the cradle member 704. When the forcer of linear motor 1302 is moved linearly forward or back, the force transmitted through the tab 1602 moves the cradle member 704 in the same direction. In some implementations, tab 1602 has a clearance in the slot 1604 to prevent over-constraint between the two linear axes of the linear motor linear slide bearing (see FIG. 15) and the linear bearing of the cradle member 704 (e.g., similar as in FIG. 11).

The use of actuators in the foot controller can provide increased flexibility to the availability, layout, and functions of paths for the cradle member 704. For example, one or more controlled actuators may be controlled to output forces to block out (remove) one or more paths altogether, or add one or more paths to the cradle member. For example, paths can be added to provide additional functions that may be available in response to particular conditions being met (e.g., a particular type of surgical procedure being performed, a particular skill level of the user, particular types of surgical instruments or slave device tools being used, etc.). In various implementations, actuators can be used to customize the foot controller operation for particular users. For example, the paths can be made shorter than a default distance (e.g., a shorter distance provided between center position and one or more activation positions) for a user who is under a threshold height or weight or having lower than a threshold size of foot, or made larger than the default distance for a user who is over a higher threshold height or weight or who has greater than a threshold size of foot. In some implementations, different resistances can be applied to the movement of the cradle member based on one or more conditions similar to those described above.

In some implementations, one or more force profiles may be incorporated into a mechanism that provides forward-back sliding and/or left-right rotating. For example, a force profile can determine the force applied in a particular degree of freedom or cradle path based on the position of the cradle member in that degree of freedom or path. Such a force profile can be used to provide passive forces (e.g., using a passive actuator such as a brake, or friction forces as described herein) and/or active forces (e.g., active motor).

In some implementations, user preferences can be used in determining haptic feedback. For example, if the user does not want assistive forces, the user may select to remove them. If a user may wants the security of keeping the pedal in one position, the user may select to apply higher forces that must be overcome between positions of the cradle member.

Figure 17:
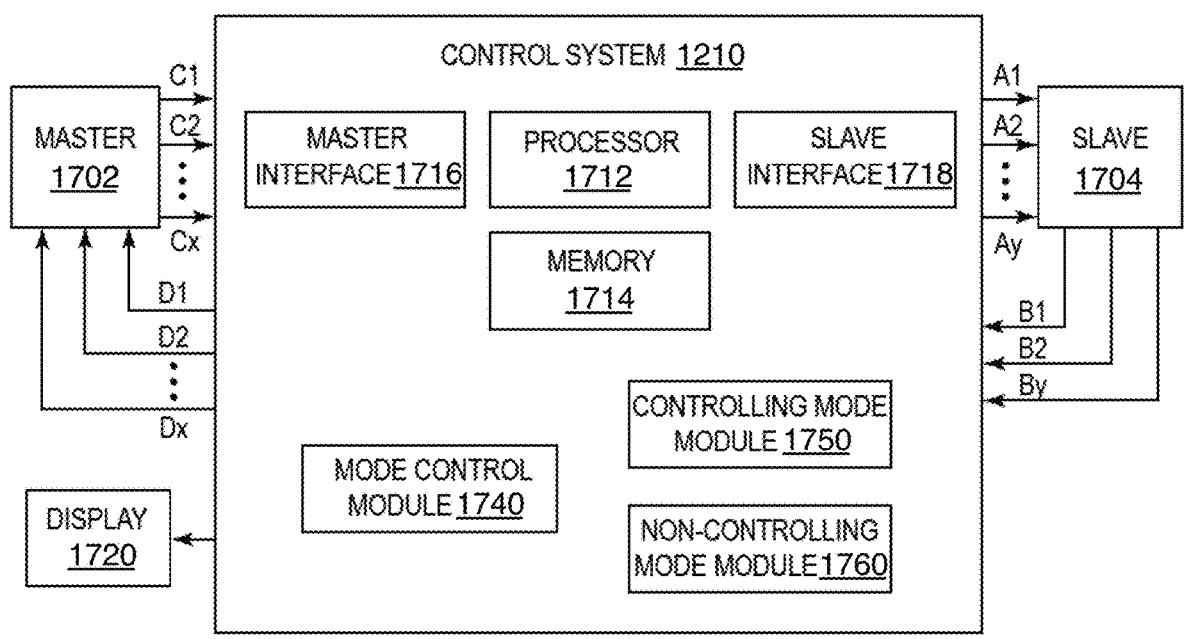
FIG. 17 is a block diagram of an example master-slave system, which can be used for one or more implementations described herein.

FIG. 17 is a block diagram of an example master-slave system 1700, which can be used for one or more implementations described herein. As shown, system 1700 includes a master device 1702 that a user may manipulate in order to control a slave device 1704 in communication with the master device 1702. More generally, master device block 1702 can include one or more of various types of devices providing one or more controllers that can be physically manipulated by a user. For example, master device 1702 can include a system of one or more master controllers such as one or more hand master controllers (e.g., hand controllers 122, 602, and 606, or other hand controllers), and one or more foot controllers (e.g., any of the foot controller implementations described herein).

Master device 1702 generates control signals C1 to Cx indicating positions, states, and/or changes of one or more controllers in their degrees of freedom. For example, the master device 1702 can generate control signals indicating selection of physical buttons, foot controller states, and other manipulations by the user.

A control system 1710 can be included in the master device 1702, in the slave device 1704, or in a separate device, e.g., an intermediary device communicatively connected between master device 1702 and slave device 1704. In some implementations, the control system 1710 can be distributed among multiple of these devices. Control system 1710 receives control signals C1 to Cx and generates actuation signals A1 to Ay, which are sent to slave device 1704. Control system 1710 can also receive sensor signals B1 to By from the slave device 1704 that indicate positions, states, and/or changes of various slave components (e.g., manipulator arm elements). Control system 1710 can include general components such as a processor 1712, memory 1714, and interface hardware 1716 and 1718 such as a master interface and a slave interface for communication with master device 1702 and slave device 1704, respectively. Processor 1712 can execute program code and control basic operations of the system 1700, and can include one or more processors of various types, including microprocessors, application specific integrated circuits (ASICs), and other electronic circuits. Memory 1714 can store instructions for execution by the processor and can include any suitable processor-readable storage medium, e.g., random access memory (RAM), read-only memory (ROM), Electrical Erasable Read-only Memory (EEPROM), Flash memory, etc. Various other input and output devices can also be coupled to the control system 1710, e.g., one or more displays 1720.

In this example, control system 1710 includes a mode control module 1740, a controlling mode module 1750, and a non-controlling mode module 1760. Other implementations can use other modules, e.g., a force output control module, sensor input signal module, etc. As used herein, the term "module" can refer to a combination of hardware (e.g., a processor such as an integrated circuit or other circuitry) and software (e.g., machine or processor executable instructions, commands, or code such as firmware, programming, or object code). A combination of hardware and software can include hardware only (i.e., a hardware element with no software elements), software hosted by hardware (e.g., software that is stored at a memory and executed or interpreted by or at a processor), or a combination of hardware and software hosted at hardware. In some implementations, the modules 1740, 1750, and 1760 can be implemented using the processor 1712 and memory 1714, e.g., program instructions stored in memory 1714 and/or other memory or storage devices connected to control system 1710.

Mode control module 1740 can detect when a user initiates a controlling mode and a non-controlling mode of the system, e.g., by user selection of controls, sensing a presence of a user at a master control workstation or master controller, sensing required manipulation of a master controller, etc. The mode control module can set the controlling mode or a non-controlling mode of the control system 1710 based on one or more control signals C1 to Cx. For example, mode control module 1740 may activate controlling mode operation if user detection module detects that a user is in proper position for use of the master controller(s) and that signals (e.g., one or more signals C1 to Cx) indicate the user has contacted the master controller(s). The mode control module 1740 may disable controlling mode if no user touch is detected on the master controller(s) and/or if a user is not in proper position for use of the master controller(s). For example, the mode control module 1740 can inform control system 710 or send information directly to controlling mode module 1750 to prevent the controlling mode module 1750 from generating actuation signals A1 to An that move slave device 1704.

In some implementations, controlling mode module 1750 may be used to control a controlling mode of control system 1710. Controlling mode module 1750 can receive control signals C1 to Cx and can generate actuation signals A1 to Ay that control actuators of the slave device 1704 and cause it to follow the movement of master device 1702, e.g., so that the movements of slave device 1704 correspond to a mapping of the movements of master device 1702. Controlling mode module 1750 can be implemented using conventional techniques.

In some implementations, controlling mode module 1750 can also be used to control forces on the controller(s) of the master device 1702 as described herein, e.g., forces output on one or more components of the master controllers, e.g., hand grip members and/or cradle member of one or more foot controllers, using one or more control signals D1 to Dx output to actuator(s) used to apply forces to the components. For example, one or more of control signals D1 to Dx can be output to one or more actuators configured to output forces to the cradle member of a foot controller as described herein, and output to one or more other actuators of the master controller, e.g., actuators configured to output forces to one or more hand controllers, actuators configured to output forces on links coupled to a master controller, etc. In some examples, control signals D1 to Dx can be used to provide haptic feedback, gravity compensation, etc.

In some implementations, a non-controlling mode module 1760 may be used to control a non-controlling mode of system 1700. In the non-controlling mode, user manipulations of master device 1702 have no effect on the movement of one or more components of slave 1704. In some examples, non-controlling mode may be used when a portion of slave 1704, e.g., a slave arm assembly, is not being controlled by master device 1702, but rather is floating in space and may be manually moved. For non-controlling mode, non-controlling mode module 1760 may allow actuator systems in the slave 1704 to be freewheeling or may generate actuation signals A1 to An, for example, to allow motors in an arm to support the expected weight of the arm against gravity, where brakes in the arm are not engaged and permit manual movement of the arm. For example, in a medical procedure, non-controlling mode may allow a surgical side assistant to easily manipulate and reposition an arm or other slave component relative to a patient or directly make some other clinically appropriate adjustment of the arm or slave component.

In some implementations, non-controlling mode can include one or more other operating modes of the control system 1710. For example, a non-controlling mode can be a selection mode in which movement of the master controller in one or more of its degrees of freedom and/or selection of controls of the master controller can control selection of displayed options, e.g., in a graphical user interface displayed by display 1720 and/or other display device. A viewing mode can allow movement of the master controller(s) to control a display provided from cameras, or movement of cameras, that may not be included in the slave device 1704. Control signals C1 to Cx can be used by the non-controlling mode module 1760 to control such elements (e.g., cursor, views, etc.) and control signals D1 to Dx can be determined by the non-controlling mode module to cause output of forces on the master controller(s) during such non-controlling modes, e.g., to indicate to the user interactions or events occurring during such modes.

Implementations described herein may be implemented, at least in part, by computer program instructions or code, which can be executed on a computer. For example, the code may be implemented by one or more digital processors (e.g., microprocessors or other processing circuitry). Instructions can be stored on a computer program product including a non-transitory computer readable medium (e.g., storage medium), where the computer readable medium can include a magnetic, optical, electromagnetic, or semiconductor storage medium including semiconductor or solid state memory, magnetic tape, a removable computer diskette, a random access memory (RAM), a read-only memory (ROM), flash memory, a rigid magnetic disk, an optical disk, a memory card, a solid-state memory drive, etc. The media may be or be included in a server or other device connected to a network such as the Internet that provides for the downloading of data and executable instructions. Alternatively, implementations can be in hardware (logic gates, etc.), or in a combination of hardware and software. Example hardware can be programmable processors (e.g. Field-Programmable Gate Array (FPGA), Complex Programmable Logic Device), general-purpose processors, graphics processors, Application Specific Integrated Circuits (ASICs), and the like.

Implementations provide various benefits. For example, a foot controller described herein can be provided with control over multiple system functions. In some implementations, the foot controller may control a variety of functions of a teleoperated slave device including, for example, camera control, swap instrument control, clutch, etc., or any combination thereof. Multiple functions can be accessed by one foot using one foot controller, where the foot can reach different activation positions without having to substantially shift weight or completely lift off the foot from the foot controller. Defined and guided paths of movement of a cradle member (e.g., pedal component moved by the user's foot) allow the user to quickly and accurately move the cradle member to desired positions and activate one or more system functions associated with those positions. Such features can provide more functions and more accurate control over such functions than previous foot pedals or other controllers.

In some implementations, such features can also reduce or eliminate the use of multiple pedals, foot switches, or other types of foot controllers and reduce the disadvantages of such multiple devices. For example, a standing user of a single foot controller having features described herein does not need to shift the user's weight to move a foot between two pedals, nor shift weight to pass control between two feet controlling two or more pedals. Use of a described foot controller also allows a standing user to move a cradle member while maintaining a foot in a moving cradle member to provide more stable and accurate control of ungrounded hand master controllers. In contrast, if a standing user uses multiple foot controllers or pedals, or needs to substantially move a single foot to access multiple pedals, there may be awkward or tiring shifting of feet for control of different pedals and/or unintentional hand master controller movement as the user shifts weight and moves his or her feet between pedals.

Features of the described foot controller allow a user's weight to be maintained on the foot controller while accessing and activating different functions. For example, the foot can be maintained in a cradle member that slides or pivots, and weight can be added on the toe to perform activations. In some pivoting implementations, a user's weight can be kept on the heel of the foot while moving the foot controller cradle member to different positions. Thus, the user experiences less fatigue by reducing or avoiding having to pick up the entire weight of the leg and foot, move it over, and plant it back down.

Furthermore, the movement of the described foot controllers may be less disruptive to a procedure being performed. For example, described implementations can reduce the need for a user to shift his or her center of gravity. For example, if a user surgeon does not pick up his or her foot and put it in new position, he or she is less likely to have to move his or her eyes down from the surgical field to look at the foot and then look up again. In some cases, a surgeon may not even be able to fully see his or her feet or foot pedals, e.g., if a base of the patient table overlaps or extends over the foot. Implementations of the described foot controller can be operated accurately if there is reduced visibility of the foot or foot controller.

There are other advantages when using a single-foot controller. For example, some users may take off their shoes at a non-sterile console so they can better feel the multiple pedals for accurate pedal selection. However, when standing next to an operating table, many surgeons want to wear shoes due to contamination issues. Thus, use of a single foot controller allows a surgeon to confidently access multiple foot control functions while wearing a shoe on the both feet. Another advantage is the reduced area occupied by a single foot controller compared to multiple pedals. This may be advantageous, for example, in a crowded operating room or other environment having multiple people and pieces of equipment.

In some implementations, the foot controller may advantageously provide haptic feedback to the user via moving components to increase accuracy of selecting cradle positions and associated functions. Haptic feedback may include resistive force and/or haptic effects output by active actuators (e.g., motors) or passive actuators or mechanisms (e.g., brakes, friction, etc.) connected to a moving portion of the foot controller. For example, haptic feedback can provide distinctive feel to each path and position of a moving foot cradle member, allowing the user to more easily distinguish different paths and activation positions for functions. Haptic feedback may cause different magnitudes of resistance to allow the user to more easily move the cradle member to different positions and/or prevent moving the cradle to undesired or inappropriate paths and positions. For example, haptic feedback can enhance safety by making it more difficult (e.g., greater opposing force or resistance) to move the cradle member to particular positions that can activate a more destructive function (e.g., a cutting or energy output function of a surgical tool), and may make it less difficult (e.g., less opposing force or resistance) to move the cradle member to other positions associated with less destructive functions (e.g., clutch, camera control, illumination control, etc.). Features can cause bias to the movement of the cradle member toward lower-energy positions. Furthermore, haptic feedback can allow different paths to different activation positions to be programmed and/or customized, e.g., activation positions and/or paths of the cradle member can be added, removed, or changed based on forces output by actuators, allowing flexibility of the foot controller to be used with different systems, applications and procedures.

Note that the functional blocks, operations, features, methods, devices, and systems described in the present disclosure may be integrated or divided into different combinations of systems, devices, and functional blocks as would be known to those skilled in the art.

Although the present implementations have been described in accordance with the examples shown, one of ordinary skill in the art will readily recognize that there can be variations to the implementations and those variations would be within the scope of the present disclosure. Accordingly, many modifications may be made by one of ordinary skill in the art without departing from the scope of the appended claims.

What is claimed is:

1. A controller comprising:
a stationary portion, a foot cradle member coupled to the stationary portion and one or more sensors, wherein:
the foot cradle member is moveable to a plurality of positions along paths within a plane,
the foot cradle member is pivotable within the plane in a pivot degree of freedom about a pivot axis that is perpendicular to the plane,
the foot cradle member is translatable within the plane in a linear degree of freedom,
one or more of the paths have a direction in the pivot degree of freedom of the foot cradle member and at least one of the paths has a direction in the linear degree of freedom of the foot cradle member,
the plurality of positions include one or more of a left position, a right position, a front position, or a back position, and
the one or more sensors are operative to sense the foot cradle member at a particular position of the plurality of positions and output one or more sensor signals indicative of the particular position, and
the one or more sensor signals cause activation of a selected function of a plurality of functions provided by a system in communication with the one or more sensors based on the particular position at which the foot cradle member is sensed.

2. The controller of claim 1, further comprising a base member coupled between the foot cradle member and the stationary portion, wherein the foot cradle member is moveable with reference to the base member in a first one of the pivot degree of freedom and the linear degree of freedom, and the base member with the foot cradle member is moveable with reference to the stationary portion in a second one of the pivot degree of freedom and the linear degree of freedom.

3. The controller of claim 2, wherein the foot cradle member is moveable with reference to the base member in the pivot degree of freedom, and the base member with the foot cradle member is moveable with reference to the stationary portion in the linear degree of freedom.

4. The controller of claim 3, wherein the base member is coupled to the stationary portion by a pivot bearing located at the pivot axis, and the foot cradle member is slidably coupled to the base member.

5. The controller of claim 2, wherein the foot cradle member is physically biased to move to a bias position of the plurality of positions by a cam and a cam roller coupled between the foot cradle member and the base member, wherein the cam contacts a sloped surface of the cam roller.

6. The controller of claim 1, wherein:
the paths are predetermined paths, and further comprising a guide engaged with the foot cradle member,
the guide limits movement of the foot cradle member in the plane to the predetermined paths, and
the guide includes slots that define the predetermined paths, the slots including a first slot having a length oriented at least partially in a forward-back direction and a second slot having a length oriented at least partially in a left-right direction.

7. The controller of claim 1, wherein the stationary portion has a varying elevation that provides a slope to the movement of the foot cradle member in at least one of the linear degree of freedom and the pivot degree of freedom.

8. The controller of claim 1, wherein two or more of the paths are each associated with a different force effect output on the foot cradle member during movement of the foot cradle member along at least a portion of the path, the force effect provided by at least one of: one or more dampers or one or more motors.

9. The controller of claim 1, wherein the foot cradle member includes at least one input control provided on a top surface of the foot cradle member.

10. The controller of claim 1, wherein the foot cradle member includes protrusions on left and right sides of the foot cradle member that extend orthogonally to a surface of the foot cradle member, and the controller further comprises:
a base member positioned between the foot cradle member and the stationary portion, the base member pivotable parallel to the plane in the pivot degree of freedom about the pivot axis with the foot cradle member; and
one or more rollers positioned at a front of the base member and contacting a surface of the stationary portion, the one or more rollers rotatable in conjunction with the pivot of the foot cradle member and the base member about the pivot axis.

11. The controller of claim 1, further comprising one or more actuators coupled to the foot cradle member, wherein the one or more actuators are controlled by the system to selectively cause output of one or more forces in one or more of the paths, the one or more forces constraining the movement of the foot cradle member to particular directions in each path.

12. The controller of claim 1, wherein the system in communication with the one or more sensors comprises a surgical system having one or more surgical instruments, and wherein the plurality of functions include at least one of:
activating a function of at least one of the one or more surgical instruments; or
switching user control between the one or more surgical instruments.

13. A system comprising:
one or more processors; and
a foot controller that includes a stationary portion, a foot cradle member, a base member coupled between the foot cradle member and the stationary portion, and one or more sensors, wherein:
the foot cradle member is constrained to move to a plurality of positions along paths within a plane,
one or more of the paths have a direction in the plane in a left-right degree of freedom of the foot cradle member and at least one of the paths has a direction in the plane in forward-back degree of freedom of the foot cradle member,
the foot cradle member is moveable with reference to the base member in the plane in a first one of the left-right degree of freedom and the forward-back degree of freedom,
the base member with the foot cradle member is moveable with reference to the stationary portion in the plane in a second one of the left-right degree of freedom and the forward-back degree of freedom,
the plurality of positions include one or more of a left position, a right position, a front position, or a back position,
one or more sensors operative to sense the foot cradle member at a particular position of the plurality of positions and output one or more sensor signals indicative of the particular position, and
the one or more sensor signals are provided to the one or more processors.

14. The system of claim 13, wherein:
the one or more sensor signals cause activation of a selected function of a plurality of functions of the system based on the particular position at which the foot cradle member is sensed,
each of the plurality of positions corresponds to one of the plurality of functions,
the plurality of functions includes a plurality of different functions, and
the foot cradle member includes an input control operative to send a control signal to the one or more processors.

15. The system of claim 13, wherein the paths are predetermined paths, wherein the foot controller further comprises a guide engaged with the foot cradle member, wherein the guide includes a plurality of slots that limit movement of the foot cradle member to the predetermined paths, wherein the plurality of slots include one or more first slots in a first alignment and one or more second slots that extend perpendicularly to and intersect with at least one of the one or more first slots.

16. The system of claim 13, wherein a restoring force physically biases the foot cradle member to move to a center position of the foot cradle member in at least one of the left-right degree of freedom or the forward-back degree of freedom, wherein the restoring force is provided by a cam mechanism coupled to the foot cradle member.

17. The system of claim 13, wherein the base member with the foot cradle member is pivotable about a pivot axis that is perpendicular to the plane, and the second one of the left-right degree of freedom and the forward-back degree of freedom is the left-right degree of freedom about the pivot axis.

18. A method comprising:
receiving a foot of a user in a foot cradle member of a controller, wherein the foot cradle member is moveable by the foot of the user within a plane into a plurality of positions including one or more of a left position, a right position, a front position, or a back position;
constraining movement of the foot cradle member to paths within the plane to the plurality of positions, wherein:
the movement of the foot cradle member includes pivoting within the plane in a pivot degree of freedom about a pivot axis that is perpendicular to the plane, and
the movement of the foot cradle member includes translation within the plane in a linear degree of freedom; and
one or more of the paths have a direction in the pivot degree of freedom of the foot cradle member and at least one of the paths has a direction in the linear degree of freedom of the foot cradle member;
sensing the foot cradle member at a particular position of the plurality of positions; and
outputting one or more sensor signals indicative of the particular position, wherein the one or more sensor signals cause activation of a selected function of a plurality of functions of a device based on the one or more sensor signals.

19. The method of claim 18, wherein constraining the movement of the foot cradle member to the paths to the plurality of positions includes constraining the movement of the foot cradle member using a guide engaged with the foot cradle member, wherein the guide includes a plurality of slots that limit movement of the foot cradle member to the paths, wherein the plurality of slots include one or more first slots in a first alignment and one or more second slots that extend perpendicularly to and intersect with at least one of the one or more first slots.

20. The method of claim 18, further comprising causing selective output of forces in at least two of the paths by one or more actuators coupled to the foot cradle member, wherein the forces provide a different force effect in each of a plurality of the at least two of the paths.

* * * * *